United States Patent
Buckner et al.

(10) Patent No.: US 7,758,491 B2
(45) Date of Patent: Jul. 20, 2010

(54) METHOD AND APPARATUS FOR THE SURGICAL TREATMENT OF CONGESTIVE HEART FAILURE

(75) Inventors: J. Kern Buckner, Littleton, CO (US); John T. M. Wright, Denver, CO (US)

(73) Assignee: Genesee BioMedical, Inc., Denver, CO (US)

( * ) Notice: Subject to any disclaimer, the term of this patent is extended or adjusted under 35 U.S.C. 154(b) by 524 days.

(21) Appl. No.: 10/599,662

(22) PCT Filed: Apr. 5, 2005

(86) PCT No.: PCT/US2005/011269

§ 371 (c)(1), (2), (4) Date: Oct. 4, 2006

(87) PCT Pub. No.: WO2005/099374

PCT Pub. Date: Oct. 27, 2005

(65) Prior Publication Data

US 2008/0027268 A1    Jan. 31, 2008

Related U.S. Application Data

(60) Provisional application No. 60/559,843, filed on Apr. 5, 2004.

(51) Int. Cl.
*A61M 1/10* (2006.01)
(52) U.S. Cl. .......................................... 600/16; 623/3.1
(58) Field of Classification Search ................... 600/16, 600/17, 37; 606/191; 623/3.17–3.23
See application file for complete search history.

(56) References Cited

U.S. PATENT DOCUMENTS

| | | | |
|---|---|---|---|
| 5,184,482 A * | 2/1993 | Cloud | 63/14.1 |
| 6,125,852 A * | 10/2000 | Stevens et al. | 128/898 |
| 6,264,602 B1 | 7/2001 | Mortier | |
| 6,494,825 B1 | 12/2002 | Talpade | |
| 6,537,198 B1 | 3/2003 | Vidlund | |
| 6,537,203 B1 | 3/2003 | Alferness | |
| 6,579,226 B2 | 6/2003 | Vanden Hoek | |

(Continued)

OTHER PUBLICATIONS

Batista (1996) J. Card. Surg. Mar.-Apr.; 11(2):96-97, "Partial Left Ventriculectomy to Improve Left Ventricular Function in End-Stage Heart Disease".

(Continued)

*Primary Examiner*—Carl H Layno
*Assistant Examiner*—Gary A Porter, Jr.
(74) *Attorney, Agent, or Firm*—Swanson & Bratschun, L.L.C.

(57) ABSTRACT

An apparatus implantable in a heart ventricle includes a frame configured to engage an inner circumferential periphery of the ventricle and to expand and contract between an expanded state corresponding to a desired end diastolic diameter of the ventricle and a contracted state corresponding to a desired end systolic diameter of the ventricle. A bistable structure is operatively associated with the frame. The bistable structure mechanically assists movement of the ventricle toward both an end systolic diameter during systole and an end diastolic diameter during diastole. The bistable structure may be integrally formed of the frame. A method of implanting the apparatus in a heart ventricle includes surgically accessing a ventricle, inserting the apparatus in the ventricle and attaching the device to a portion of myocardium defining an inner circumferential periphery of the ventricle.

20 Claims, 22 Drawing Sheets

U.S. PATENT DOCUMENTS

| | | |
|---|---|---|
| 6,582,355 B2 | 6/2003 | Alferness |
| 2003/0023132 A1 | 1/2003 | Melvin |
| 2003/0158570 A1* | 8/2003 | Ferrazzi .................. 606/191 |
| 2004/0002262 A1 | 1/2004 | Feld |

OTHER PUBLICATIONS

Braunwald ed. (1992) *Heart Disease: A Textbook of Cardiovascular Medicine, 4th edition*. W.B. Saunders and Company, Philadelphia, p. 370-382.

Gregoric and Couto (2002) Congestive Heart Failure 8:214-219, "Surgical Treatment of Congestive Heart Failure".

Nemeh and Smedira (2003) Cleveland Clinic Journal of Medicine 70:223-233, "Mechanical Treatment of Heart Failure: the Growing Role of LVADs and Artificial Hearts".

Starling (1998) Cleveland Clinic Journal of Medicine 65:351-358, "The Heart Failure Pandemic: Changing Patterns, Costs, and Treatment Strategies".

Westaby (1996) Heart 76:200-206, "The Need for Artificial Hearts".

\* cited by examiner

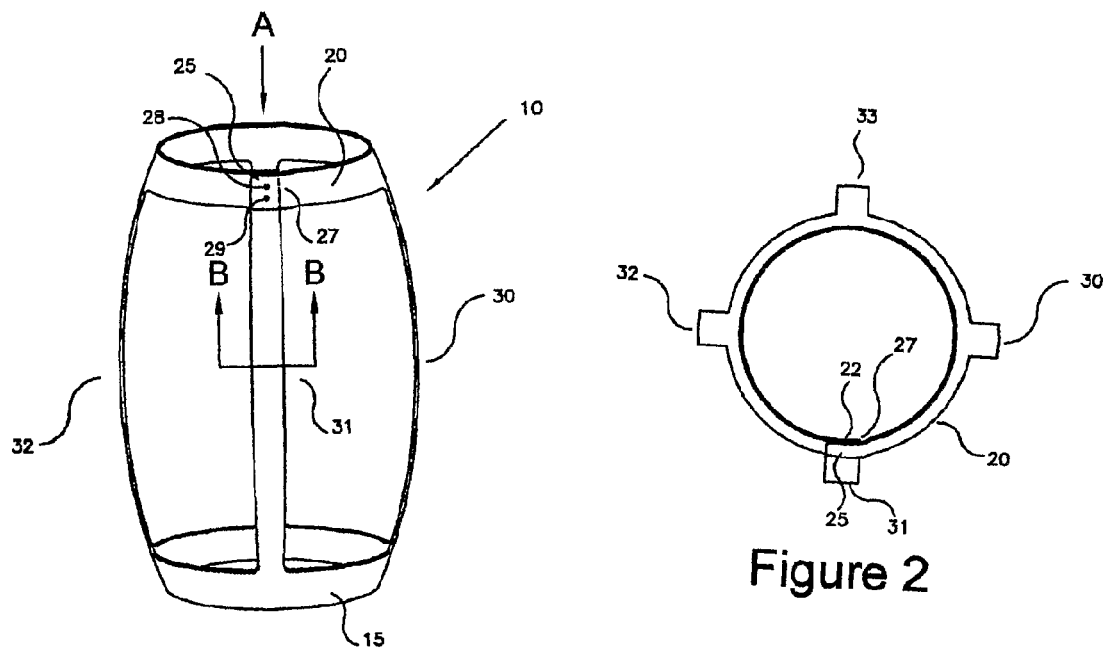
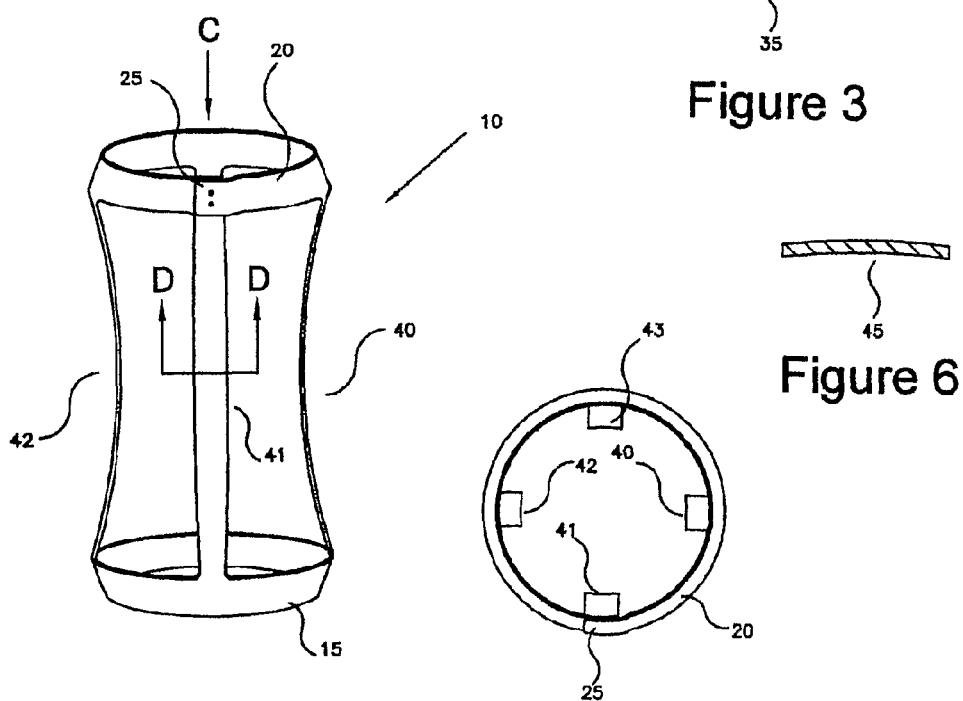
Figure 1
Figure 2
Figure 3
Figure 4
Figure 5
Figure 6

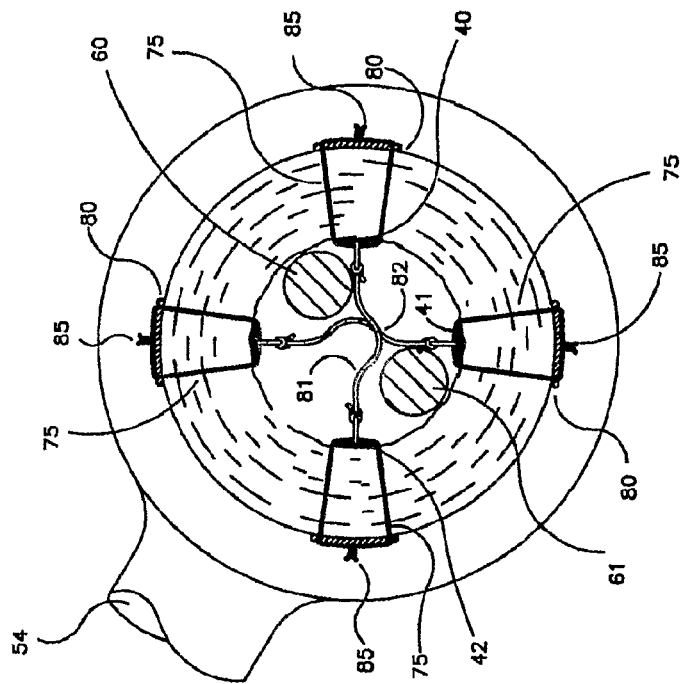
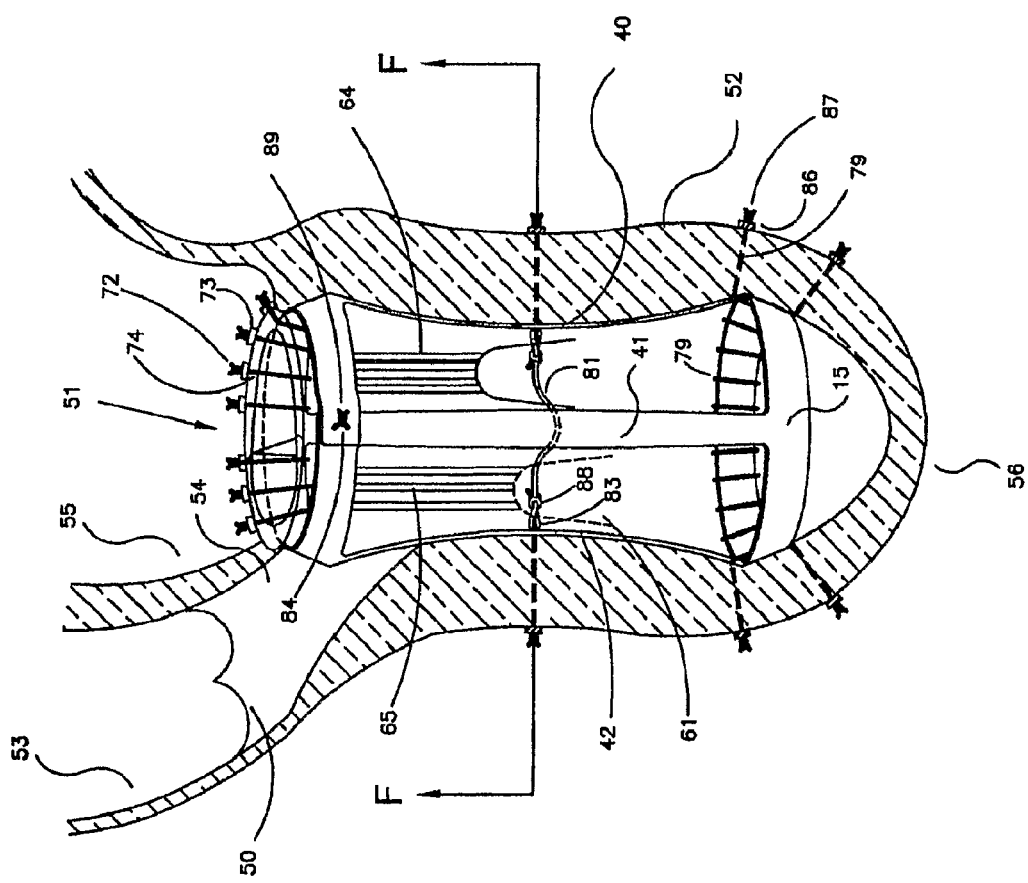
Figure 10
Figure 9

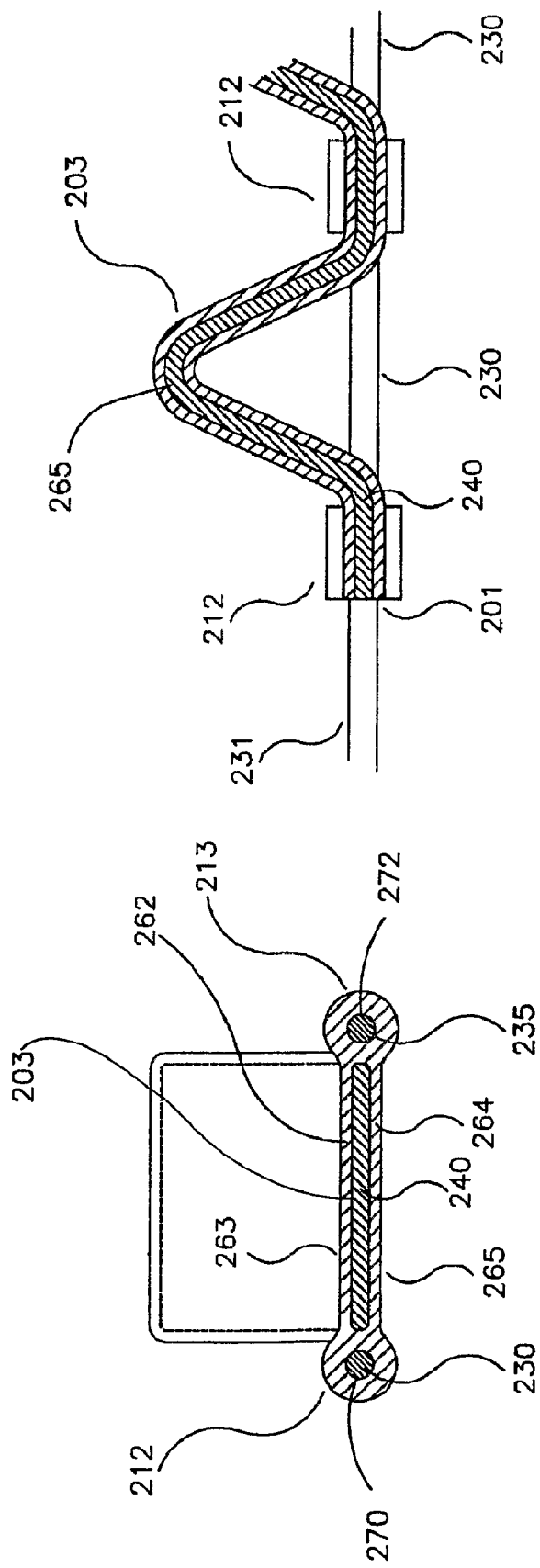

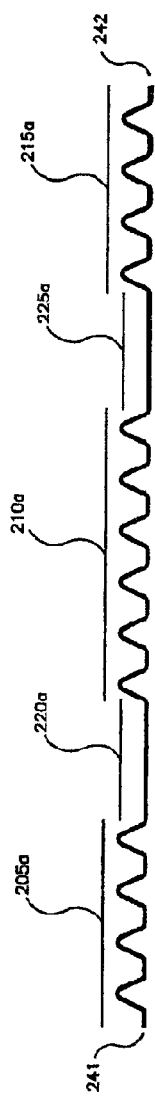
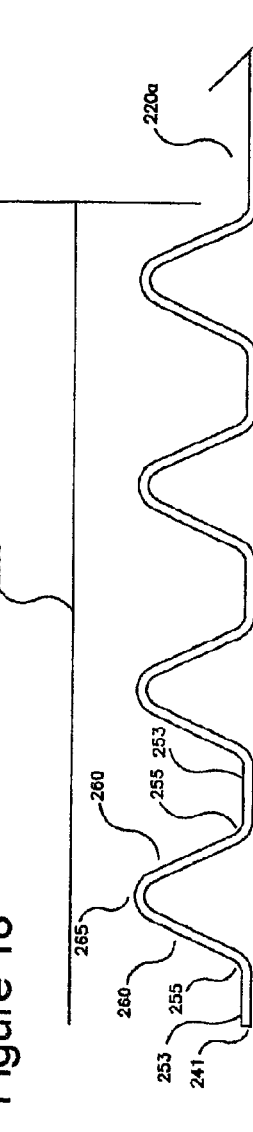
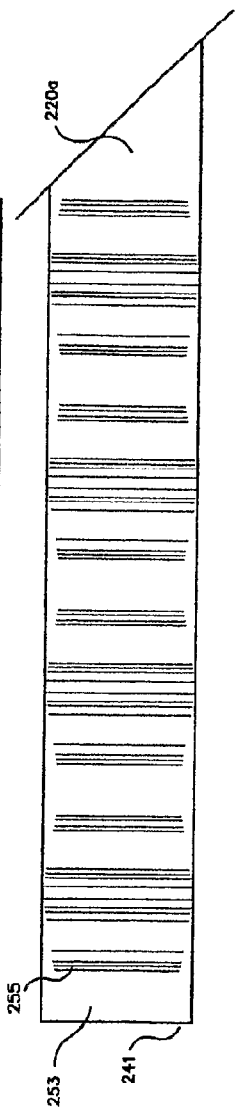
Figure 17
Figure 18
Figure 19
Figure 20

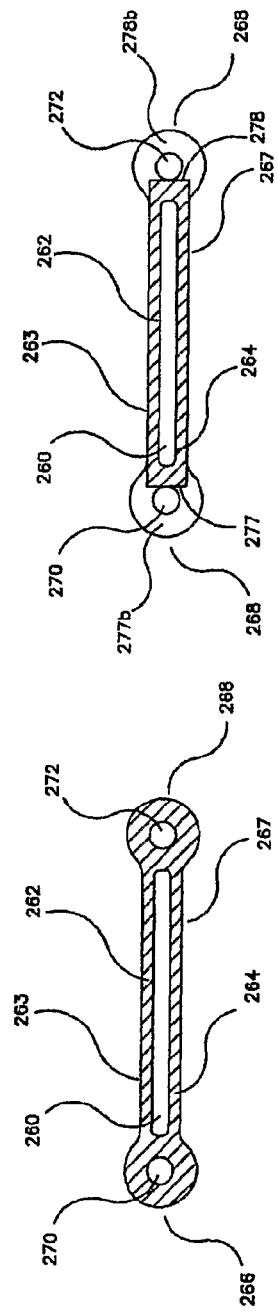
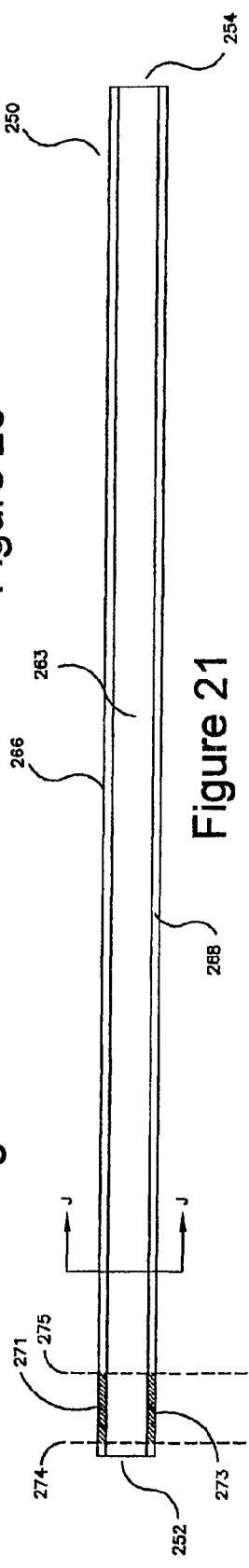
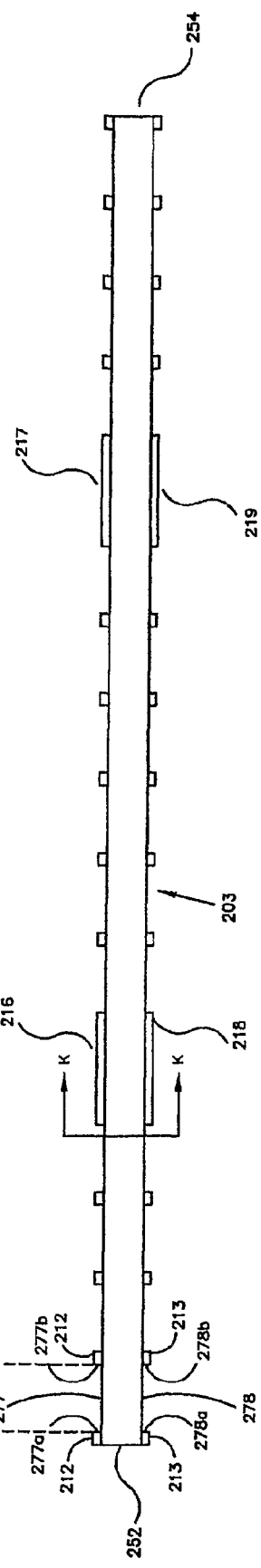

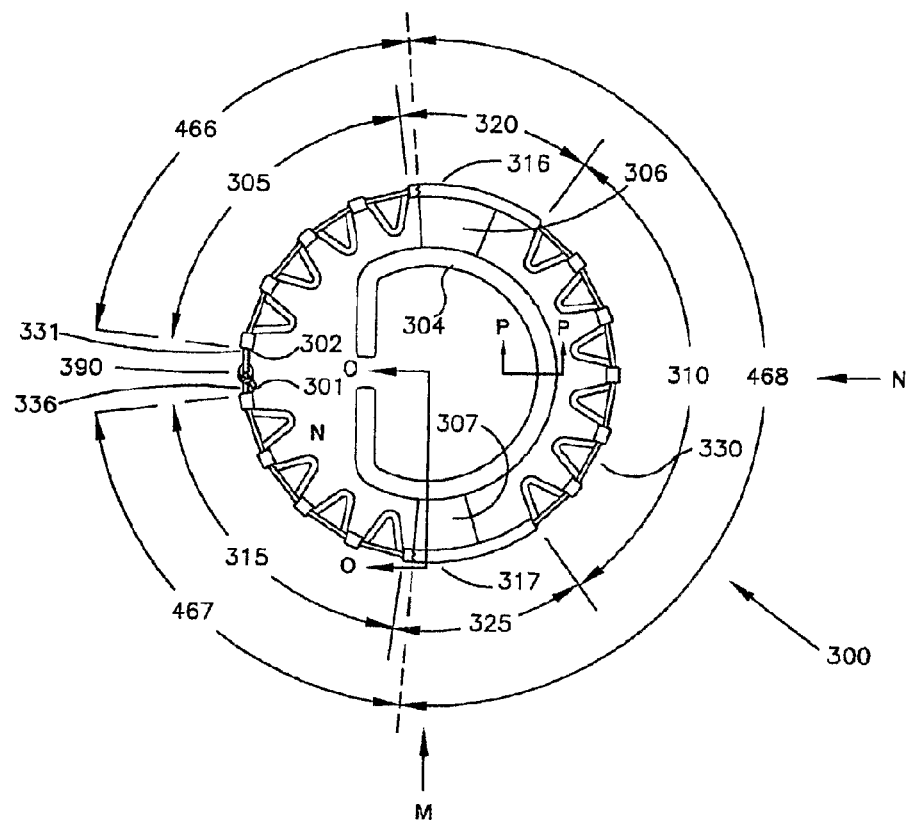
Figure 30
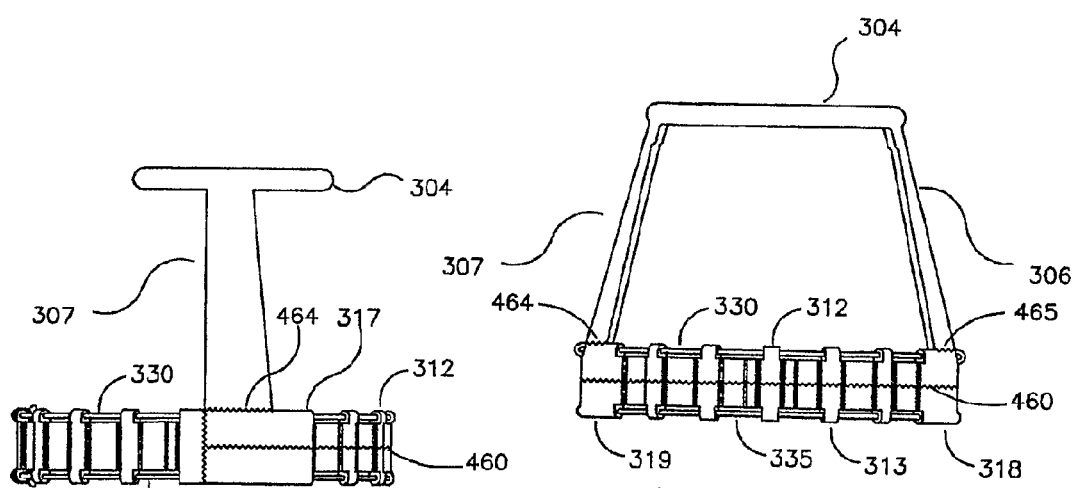
Figure 31
Figure 32

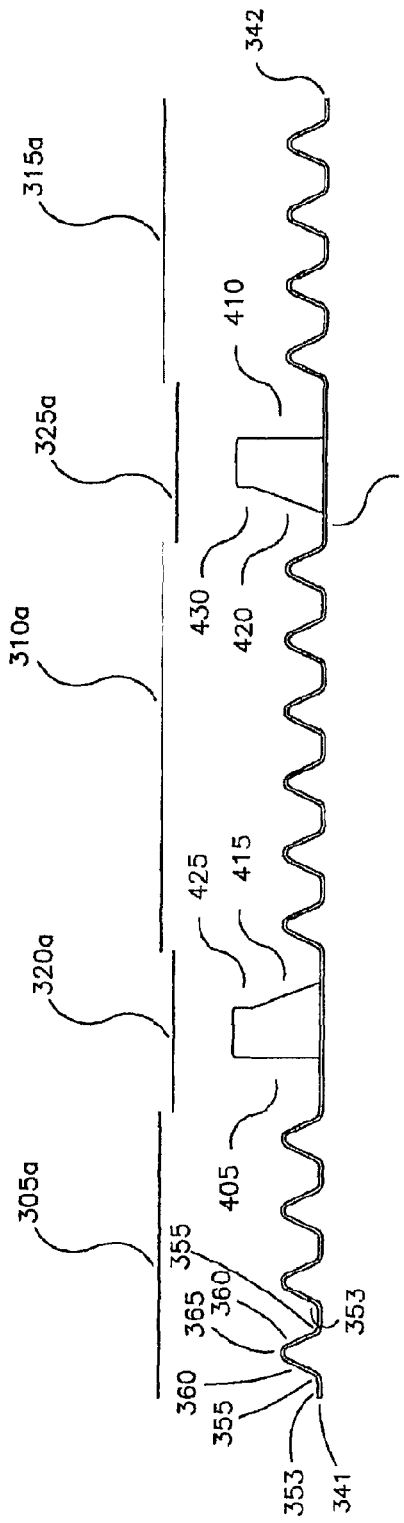
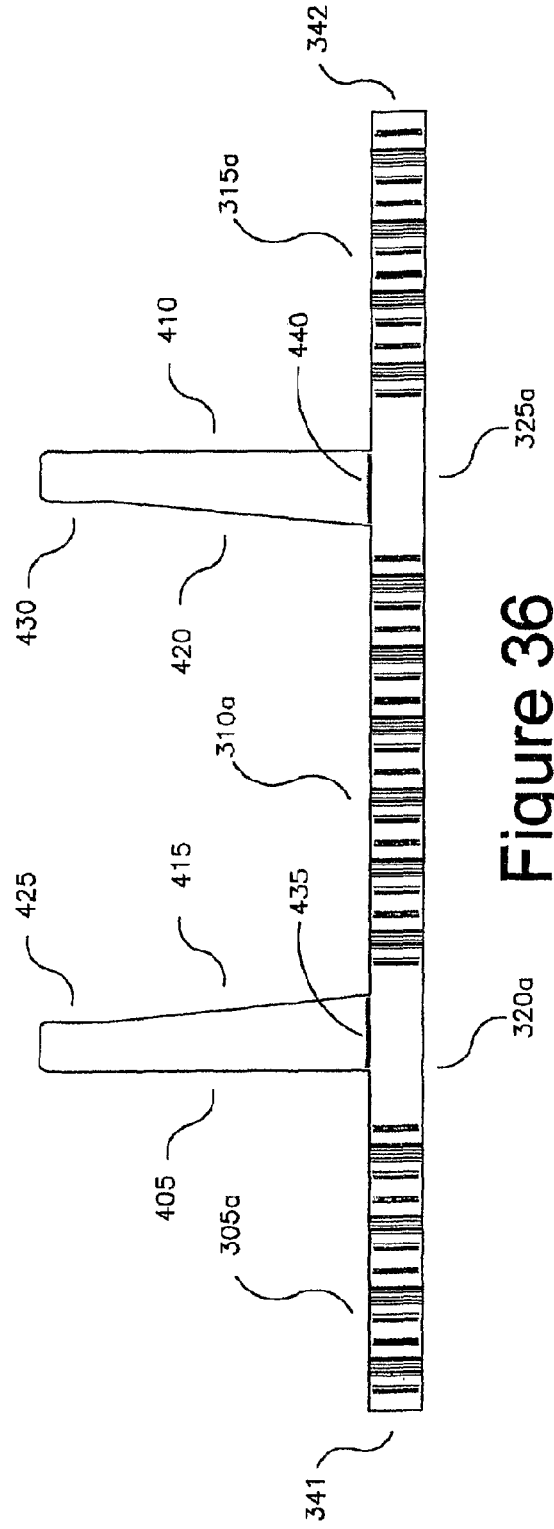
Figure 35
Figure 36

METHOD AND APPARATUS FOR THE SURGICAL TREATMENT OF CONGESTIVE HEART FAILURE

RELATED APPLICATIONS

This application is a 35 U.S.C. §371 national phase application of PCT/US05/011269 (WO 2005/099374), filed on Apr. 5, 2005, entitled "Method and Apparatus for the Surgical Treatment of Congestive Heart Failure," which application claims priority to U.S. Provisional Application Ser. No. 60/559,843, filed Apr. 5, 2004, each of which is incorporated herein by reference in its entirety.

BACKGROUND OF THE INVENTION

Congestive Heart failure is defined as the failure of the heart to pump blood at a rate to satisfy the requirements of metabolizing tissues. Heart failure is the manifestation of many disease processes affecting the heart and the great vessels, including ischemic cardiomyopathy, viral cardiomyopathy, metabolic or toxic cardiomyopathy and idiopathic cardiomyopathy. Many of these disease processes lead to dilation of the left ventricle as an initial adaptive or compensatory mechanism. This is a short-lived adaptation due to the impaired contractile function of the heart with an inappropriate thinning of myocardium rather than appropriate thickening and, thereby, leading to further left ventricle dilation and cardiac deterioration.

Congestive heart failure is a leading cause of death in the United States. With the aging of the population (baby boomers) and the advent of improved cardiovascular therapies, the incidence of congestive heart failure is increasing. Congestive heart failure is most prevalent in people of age 65 or older (incidence 3/1,000 in men age 50-59 and 27/1000 in men age 80-89) and, by 2030, it is estimated that heart failure prevalence will double to 5.7 million cases annually, thereby reaching pandemic proportions. See Starling (1998) *The Heart Failure Pandemic: Changing Patterns, Cost, and Treatment Strategies*. Cleveland Clinic Journal of Medicine, 65:351-358. Within the next ten years it is estimated that 70 million Americans will suffer from congestive heart failure.

As the disease of congestive heart failure progresses the left ventricle further dilates, and the myocardial wall thickness is further diminished. In addition, the left ventricle becomes more spherical and less episoidal, the distance between the papillary muscles and the mitral annulus increases, and the mitral annulus enlarges, especially in the anterior/posterior direction resulting in significant mitral regurgitation. The thinning of the left ventricular myocardium significantly and progressively raises the stress level in the left ventricular wall such that left ventricle function is diminished and eventually ceases to provide sufficient cardiac output to sustain life, resulting in the demise of the patient.

Typically in congestive heart disease the internal diameter of the ventricle increases over time and the left ventricular wall thickness decrease over time. In some patients the systolic pressure increases due to systemic hypertension or aortic stenosis. A similar scenario occurs, but for different reasons, in patients with mitral valve regurgitation and concomitant aortic stenosis or systemic hypertension.

In the last two decades there have been significant advances in medical management of congestive heart failure. However, despite these significant improvements in clinical outcomes (death and quality of life) of congestive heart failure, these therapies are limited and as the disease relentlessly progresses the patient either needs to receive a cardiac transplant or will die. Cardiac transplantation presently is the treatment of choice for medically refractory congestive heart failure. Donor organ shortages and patient selection (eligibility) limit this therapy to only a relatively low percentage of patients.

Several problems face the clinician in treating patients with congestive heart failure. The first concern is the determination of how far the disease has progressed. The second concerns when the patient has become a viable candidate for surgery, either for cardiac transplantation or alternative surgical intervention.

Preload (length of stretch of sarcomere at end of diastole) and after load (wall stress during ventricular ejection) are interdependent and physiologic components of heart function. See Braunwald ed., (1992) *Heart Disease: A Textbook of Cardiovascular Medicine, 4th edition*. W.B. Saunders and Company, Philadelphia, p. 370-382. Many pharmacological therapies have targeted their efficacy on these parameters by reducing ventricular volumes or cardiac and systemic pressures while other therapies alter the inotropic (contractile force) function of the heart. Medical therapy (neuroendocrine axis, improved expression of contractile proteins, enhanced cellular respiratory control, and decrease in markers of apoptosis and cellular stress) however, has had limited success, not only with the management of symptoms but also in achieving long-term survival benefit.

In an attempt to counter the progression of congestive heart failure, in 1996 Batista, recognizing the relentless progression of the disease, described a surgical procedure in which a segment of the left ventricle was removed, thus reducing the overall internal diameter of the heart. See J. Card. Surg. 1996 March-April; 11(2):96-7. Of course, the operative procedure also removed a segment of potentially contractile myocardium, reducing the overall contractive potential of the heart as a whole.

Presently, surgical intervention generally consists of a surgical remodeling of the left ventricle to reduce its end-diastolic volume and attempting to re-convert the abnormal spherical shaped ventricle to the near normal elipisoidal shaped ventricle. However, this usually means the implantation of an akinetic ventricular patch, so the patient's ventricular ejection fraction is seldom normal following surgery. In patients where the mitral annulus has become greatly distorted, usually by elongation, it is necessary to implant a rigid type mitral annuloplasty ring. This surgery, although helpful in some patients, is not fully effective.

End diastolic external cardiac restricting devices have been used in an attempt to prevent spherical distortion or enlargement of ventricles. For example, Acorn Cardiovascular, Inc. sells CorCap™, an endocardial support device, which is a mesh-like heart "jacket" that is placed around the heart and held in place to prevent any further enlargement (See U.S. Pat. Nos. 6,582,355; 6,579,226; 6,537,203). This and similar devices, although providing immediately post-operative effective relief for the patient, may lead to long term constrictive pericarditis in a significant number of patients. Another end diastolic restricting device has been proposed by Vidlund R M et al. (See U.S. Pat. No. 6,537,198). This patent discloses using one or more cables passed through opposing portions of the myocardial wall and across the ventricular cavity to exit the opposing myocardial wall. Ends of the cable are intended to be secured using crimped "buttons". This proposed method may not provide sufficient myocardial support to the heart.

Alternative mechanical devices are, therefore, necessary and needed. See Gregoric and Couto (2002) *Surgical Treatment of Congestive Heart Failure, Congestive Heart Failure,*

8:214-219 Many end-stage congestive heart failure patients may, therefore, benefit from a mechanical device, either as a bridge to transplant or as destination therapy, if they are otherwise ineligible for transplant. See Nemeh and Smedira (2003) *Mechanical Treatment of Heart Failure: The Growing Role of LVADs and Artificial Hearts*, Cleveland Clinic Journal of Medicine 70:223-233; see also Westaby (1996) *The Need for Artificial Hearts*, Heart, 76:200-206.

Each of the foregoing patents and publications is incorporated herein by reference in its entirety. The present invention is intended to address one or more of the problems discussed herein.

SUMMARY OF THE INVENTION

A first aspect of the invention is an apparatus implantable in a heart ventricle. The apparatus includes a frame configured to engage an inner circumferential periphery of a ventricle and to expand and contract between an expanded state corresponding to a desired end diastolic diameter of the ventricle and a contracted state corresponding to a desired end systolic diameter of the ventricle. Assisting means are operatively associated with the frame for mechanically assisting movement of the ventricle toward at least one of an end systolic diameter during systole and an end diastolic diameter during diastole. In one embodiment the assisting means assists movement of the ventricle toward both end systolic diameter during systole and diastolic diameter during diastole. In another embodiment the assisting means assists movement of the ventricle toward only end diastolic diameter during diastole. In either of these embodiments, the assisting means is integrally formed with the frame.

The frame may comprise a bistable element having a contracted stable state and an expanded stable state corresponding to a desired end systolic diameter and an end diastolic diameter. The bistable element may comprise a plurality of longitudinal bands each having a top and a bottom end, the top ends of the longitudinal bands being joined by a top circumferential band extending therebetween and the bottom ends of the longitudinal bands being joined by a bottom circumferential band extending therebetween. The bistable nature of the bistable element may be provided by the longitudinal bands having a concave cross-section relative to an inner surface of the bands with the bistable element in the expanded state and in the contracted state the longitudinal bands having a convex cross-section relative to the inner surface of the bands. In such an embodiment the longitudinal bands may be made of memory metal to ensure their resiliency. In a further embodiment of the bistable element, the top circumferential band joining the top ends of the longitudinal bands is split across its circumference and the top band is self biased to define a space between adjacent ends of the split. A tie is provided for connecting the ends adjacent to the split to define a substantially circular top band. The self-biasing means may be configured to self-bias between the expanded and contracted bistable states when circumferentially deflected beyond a select point toward the other of the bistable states.

In another embodiment of the bistable element, a mitral annuloplasty ring extends axially from the top of the bistable element, the bistable element and the mitral annuloplasty ring being configured so that with the bistable element attached to the myocardium defining the inner circumferential periphery of a left ventricle, the mitral annuloplasty ring is below but proximate the mitral annulus. The mitral annuloplasty ring may define a "C" shape and the top and bottom circumferential bands may be split to also define a "C" shape with the mitral annuloplasty ring and the circumferential bands axially aligned.

In an embodiment useful for maintaining the ventricle in a desired elliptical shape, the frame has a generally elliptical profile in the expanded state and a generally hourglass profile in the contracted state which generally confirm to an ideal end diastolic and an systolic ventricle shape, respectively.

In yet another embodiment of the invention, the frame and the assisting means may include a resilient band, a spring operatively associated axially with the resilient band and a tie for joining the ends of the resilient band into a circle. The resilient band is configured, with the ends joined, to engage an inner circumferential periphery of a ventricle with the spring element in a relaxed state during one of an end diastolic or a systolic state of the ventricle. In one preferred from, the spring element is integrally formed with the resilient band. The spring element may comprise concertina shaped deformations in the resilient band. Where desired, a biocompatible sheath receives the resilient band. The biocompatible sheath may comprise a plurality of lengthwise tubes and a ligature fed through the lengthwise tubes of the sheath. The ligatures may be tied to together to act as the means for joining the ends of the resilient band into a circle. A mitral annuloplasty ring may be provided extending axially of the resilient band, with the resilient band formed into a circle. The mitral annuloplasty ring may be attached by two legs to the resilient band. The mitral annuloplasty ring may be substantially "C" shaped.

Another aspect of the invention is a method of treating cardiac disease. The method includes surgically accessing a ventricle and inserting within the ventricle an apparatus configured to mechanically assist movement of the ventricle toward at least one of an end systolic diameter during systole and an end diastolic diameter during diastole. The device is attached to a portion of the myocardium defining an inner circumferential periphery of the ventricle.

In one embodiment the apparatus is a bistable apparatus configured to engage the inner circumferential periphery of the ventricle. The bistable element has a contracted stable state and an expanded stable state corresponding to an end systolic diameter and an end diastolic diameter, respectively. The bistable element may include a plurality of longitudinal bands each having a top and a bottom end, the top ends of the longitudinal bands being joined by a circumferential band extending therebetween, and the bottom ends of the longitudinal bands being joined by a bottom circumferential band extending therebetween. The top circumferential band joining the top ends of the longitudinal band is split across its circumference and self biased to define the space between adjacent ends of the split. This embodiment of the method further includes during the inserting step, passing the chordae tendineae through the space between the ends adjacent to the split and attaching the adjacent ends together to form the top band into a circle. With this embodiment, the method further includes attaching the longitudinal bands to the inner circumferential periphery of the ventricle, attaching the top circumferential band to the myocardium proximate the mitral annulus and attaching the bottom circumferential band to the myocardium proximate the ventricle apex. A mitral annuloplasty ring may be provided extending axially from the top circumferential band. In this embodiment the bistable element and the mitral annuloplasty ring are configured so that with the bistable element attached to the myocardium defining the inner circumferential periphery of the left ventricle, the mitral annuloplasty ring is below but proximate the mitral annulus. The mitral annuloplasty ring is attached to the myocardium subannularly proximate the mitral annulus.

In another embodiment of this aspect, the apparatus comprises a resilient band having at least one spring element operatively associated axially with the resilient band to allow axial stretching and compression of the resilient band. The inserting step further comprises placing the resilient band into contact with the inner circumferential periphery of the ventricle and forming the resilient band into a loop of a diameter about equal to an end diastolic diameter of an inner circumferential periphery of the ventricle. The attaching step is performed by placing the circumferentially spaced sutures in engagement with the resilient band and passing the sutures through the ventricle. The resilient band may include at least one circumferential ligature operatively associated with the resilient band, the circumferential ligature having opposing free ends. The method further includes forming the resilient band into a loop by tying the opposing free ends of the ligature together. Where this aspect of the invention is practiced with a left ventricle, the method may further include placing the resilient band into contact with the inner circumferential periphery of the left ventricle proximate the papillary muscles. In addition, while inserting the resilient band into the ventricle, the chordae tendineae are received with the resilient band as it is placed into contact with the inner circumferential periphery of the left ventricle. In using this embodiment, the method may further include performing surgical ventricular reduction prior to the inserting step. The method may further include placing a portion of a trained latissimus dorsae muscle around the band within the heart. Alternatively, a portion of a trained latissimus dorsae muscle maybe wrapped outside the ventricle about the inner circumferential periphery of the left ventricle. The resilient band may further comprise a mitral annuloplasty ring extending axially of the resilient band with the resilient band formed into a circle. In such an embodiment the method further includes attaching the mitral annuloplasty ring to the myocardium below but proximal the mitral annulus.

Yet another aspect of the invention is a bistable element implantable in a heart ventricle, the bistable element being configured to engage an inner circumferential periphery of the ventricle and having a contracted stable state and an expanded stable state corresponding to a desired end systolic diameter and a diastolic diameter. The bistable element may include a plurality of longitudinal bands each having a top and a bottom end, the top ends of the longitudinal bands being joined by a top circumferential band extending therebetween and the bottom ends of the longitudinal bands being joined by a bottom circumferential band. In this embodiment the bistable element has a generally elliptical profile in the expanded state and a generally hour-glass profile in the contracted state, generally conforming to an ideal ventricle shape during diastole and systole, respectively.

A further aspect of the invention is a method of augmenting systolic contraction and diastolic relaxation of a heart ventricle. The method includes providing a bistable element configured to engage an inner circumferential periphery of a ventricle, the bistable element having a contracted stable state and an expanded stable state corresponding to a desired end systolic diameter and an diastolic diameter. The ventricle is surgically accessed and the bistable element is inserted within the ventricle. The bistable element is attached to a portion of the myocardium defining an inner circumferential periphery of the ventricle.

Another aspect of the invention is an apparatus implantable in a heart ventricle, the apparatus including a resilient band and a spring operatively associated axially with the resilient band. A clasp is provided for joining the ends of the resilient band into a circle. The resilient band is configured, with the ends joined, to engage an inner circumferential periphery of a ventricle with the spring element in a relaxed state during diastole of the ventricle. A biocompatible sheath may be provided around the resilient band and the spring element. The spring element may be integrally formed of the resilient band. Means may be provided for limiting the diameter of the resilient band during diastole. A mitral annuloplasty ring may be provided extending axially of the resilient band with the resilient band formed into a circle. At least two legs may join the mitral annuloplasty ring to the resilient band.

Yet another aspect of the invention is a method of treating cardiac disease using the implantable apparatus described in the preceding paragraph. The method includes surgically accessing a ventricle of the heart, placing the resilient band into contact with the inner circumferential periphery of the ventricle, forming the resilient band into a diameter about equal to an end diastolic diameter of the inner circumferential periphery of the ventricle and attaching the resilient band loop to the myocardium defining the inner circumferential periphery of the ventricle. The resilient band may be placed into contact with the inner circumferential periphery of the left ventricle proximate the papillary muscles. In this embodiment, the chordae tendineae are received within the resilient band as the resilient band is placed into contact with the inner circumferential periphery of the left ventricle. The method may further include performing a surgical ventricular reduction before inserting the resilient band into the ventricle. A portion of trained latissimus dorsae muscle may be wrapped around the band within the heart. Electrodes of a pacemaker may be brought into electric communication with the latissimus dorsae muscles. In another embodiment, a portion of the latissimus dorsae muscle is wrapped outside the ventricle outside the inner circumferential periphery of the ventricle. This embodiment may also include placing electrodes of a pace maker into electric communication with the latissimus dorsae muscle. The resilient band may further include a mitral annuloplasty ring extending axially of the resilient band with the resilient band formed into a circle. In such an embodiment the method would further include, while the left ventricle is surgically accessed, attaching the mitral annuloplasty ring to the myocardium below but proximate the mitral annulus.

The various aspects of the present invention provide methods and apparatus for the treatment of congestive heart failure. The aspects of the bistable element with the longitudinal and circumferential bands provide a device that can be surgically attached within the ventricle to maintain the desired shape of the ventricle. In addition, this aspect allows mechanical assist to the ventricle during diastole and systole. The aspect comprising a resilient band and spring also provides mechanical assist to the ventricle during either diastole or systole and can help maintain a desired shape of the ventricle. The methods for implanting the device provide an effective means of treating cardiac disease at far less cost than more invasive methods such as heart transplant. Alternatively, the devices and method may be used as a stop-gap while the patient awaits a heart transplant as a more permanent solution to congestive heart failure. The simplicity and design of the inter-ventricular devices of the invention are such that they are relatively inexpensive to manufacture, relative to the long-term cost of treating patients with congestive heart failure.

BRIEF DESCRIPTION OF THE DRAWINGS

FIG. 1 is an isometric view of a first embodiment of an apparatus implantable in a heart ventricle for providing mechanical assist comprising a bistable element in a first bistable or expanded stable state.

FIG. 2 is a plan view of the bistable element of FIG. 1 taken in the direction of arrow A in FIG. 1.

FIG. 3 is a part cross-section taken along line BB of FIG. 1.

FIG. 4 is an isometric view of the bistable element of FIG. 1 in a second bi-stable or contracted stable state.

FIG. 5 is a plan view of the bistable element of FIG. 4 taken in the direction of arrow C in FIG. 4.

FIG. 6 is a part cross-section taken along line DD of FIG. 4.

FIG. 9 is a cross-sectional view of a left ventricle of a heart at initial diastole with the embodiment of the bistable element of FIGS. 1-6 implanted within the ventricle.

FIG. 10 is a cross-sectional view of the left ventricle view of the heart at initial diastole taken along line FF of FIG. 9.

FIG. 15 is an enlarged cross-sectional view of the implantable spring band of FIG. 13 taken in the direction of the line HH of FIG. 13.

FIG. 16 is an enlarged part cross-sectional view of the implantable spring band of FIG. 13 taken in the direction of line II in FIG. 14.

FIG. 17 is a side elevation view of the implantable spring band of FIG. 13 with a sheath removed.

FIG. 18 is a plan view of the implantable spring band of FIG. 17.

FIG. 19 is an enlarged side elevation view of the implantable spring of FIG. 17.

FIG. 20 is an enlarged plan view of the implantable spring band of FIG. 18.

FIG. 21 is a plan view of an extruded sheath.

FIG. 22 is an enlarged cross-sectional view of the extruded sheath taken direction of the arrows JJ of FIG. 21.

FIG. 23 is an enlarged cross-sectional view of the extruded sheath taken in the direction of the arrows KK of FIG. 24.

FIG. 24 is a plan view of the extruded sheath of FIG. 21 following the removal of surplus side material.

FIG. 30 is a plan elevation of an alternative embodiment of the implantable spring band incorporating a sub-annular mitral annuloplasty ring. The device has been closed and ligatures tied simulating its implanted configuration.

FIG. 31 is a side elevation view of the alternative embodiment of the implantable spring band taken in the direction of arrow M in FIG. 30.

FIG. 32 is a side elevation of the alternative embodiment of the implantable spring band taken in the direction of arrow N in FIG. 30.

FIG. 35 is a side elevation view of the alternative embodiment of the implantable spring band incorporating a sub-annular mitral annuloplasty shown ring FIG. 30, prior to the forming of the hoop shown in FIG. 30.

FIG. 36 is an elevation view of a portion of the implantable spring band of FIG. 35.

DETAILED DESCRIPTION OF THE INVENTIONS

Figure 7:
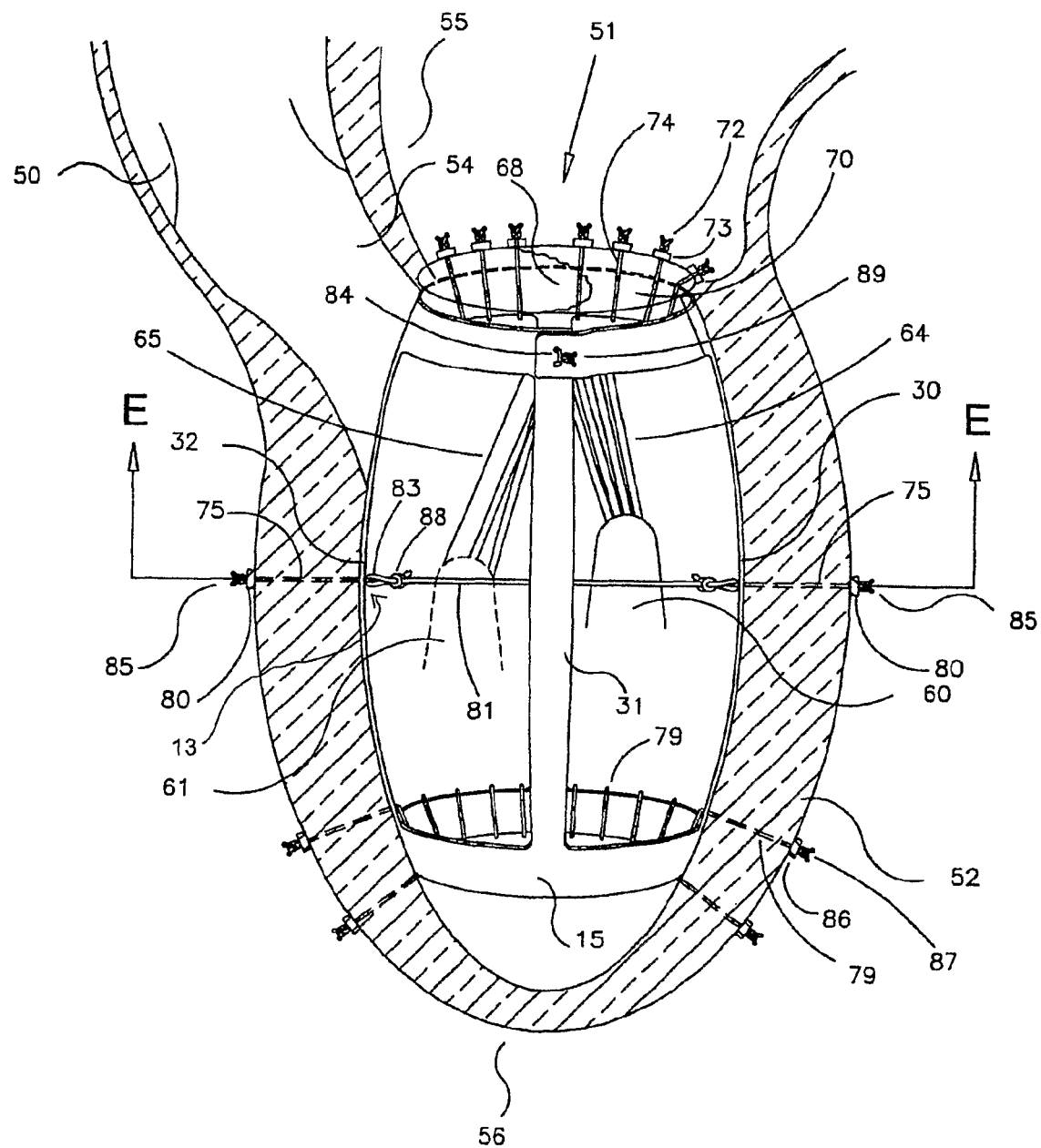
FIG. 7 is a cross-sectional view of a left ventricle of a heart at initial systole with the embodiment of the bistable element of FIGS. 1-6 implanted within the ventricle.

Referring now to the drawings wherein like numerals indicate like elements, the various embodiments of the invention will now be described in more detail. Note that in the following embodiments of the invention, the left ventricle is used as an example of where the embodiments are deployed. It will be understood by one skilled in the art that the methods and devices of the invention may also be readily used in the right ventricle, or in both ventricles.

FIG. 1 is an isometric view of a first embodiment of an apparatus implantable in a heart ventricle for providing mechanical assist to the operation of the ventricle. The first embodiment is a bistable element 10 comprising a frame implantable in a heart ventricle. A specific example of an embodiment of the bistable element 10 is in the form of a frame shaped as a bistable cage shown in an expanded condition. FIG. 2 is a plan view taken in the direction of arrow A of FIG. 1. The frame or cage is bounded at its lower end by a bottom circumferential band or hoop 15 and at the upper end by a top circumferential band in the form of an overlapping open hoop 20. An overlapping end portion 25 (which overlaps end portion 22) of the top circumferential band 20 allows the overlapping end portion 25 to be sprung open. As described below, this feature allows the chordae tendineae to be passed into the cage during implantation. Holes 28, 29 in overlapping end portion 25 have corresponding holes (not shown) in end portion 22 through which a suture may be passed to retain the upper hoop closed at implantation. In one embodiment of the invention the cage or frame further comprises four curved longitudinal bands 30, 31, 32, 33, each having a top and a bottom secured by the top and bottom circumferential bands respectively. The longitudinal bands are shown in an expanded stable state in FIGS. 1 and 2. Those skilled in the art will recognize that two, three, five, six or more longitudinal struts could be used. The dimensions of the bistable cage, including the length, annular diameter, apical diameter, and degree of curvature will vary depending upon individual patient's anatomy and pathology. The upper vertical edge 27 of longitudinal band 30 lies behind overlapping end portion 25 of upper circumferential band 20.

The cage material is formed during manufacture to be mechanically bistable. In one embodiment the bistable property of the cage results from a characteristic curved cross-section of the limbs of the cage (see FIG. 3).

FIG. 4 shows the bistable cage 10 in its contracted stable state. The four curved longitudinal strut members 40, 41, 42, 43 have undergone a change of state from the generally elliptical convex barrel like profile shown in FIG. 1 to a concave hour-glass profile shown in FIG. 4. FIG. 6 is a cross-section taken along line DD of FIG. 4. The slight convex outer curve 35 shown in FIG. 3 has transformed into a slight concave curve 45 shown in FIG. 6 to maintain the bistable cage 10 in the contracted stable state. The bands of the bistable element may comprise materials including but not limited to metals or alloys such as Nickel Titanium alloy, stainless steel, Titanium, or other similar property metals; or the bands may comprise laminates or other materials having similar hard and flexible characteristics to such metals and alloys. In one example, the bands comprise super elastic grade Nickel Titanium alloy (a super elastic "memory metal" depending upon its composition and heat treatment conditions) otherwise known as "Nitinol." The bands may be comprised of simple strips, or comprise of a bundle of monofilaments arranged optimally in rectangular circular elliptical or other suitable cross-section.

Figure 8:
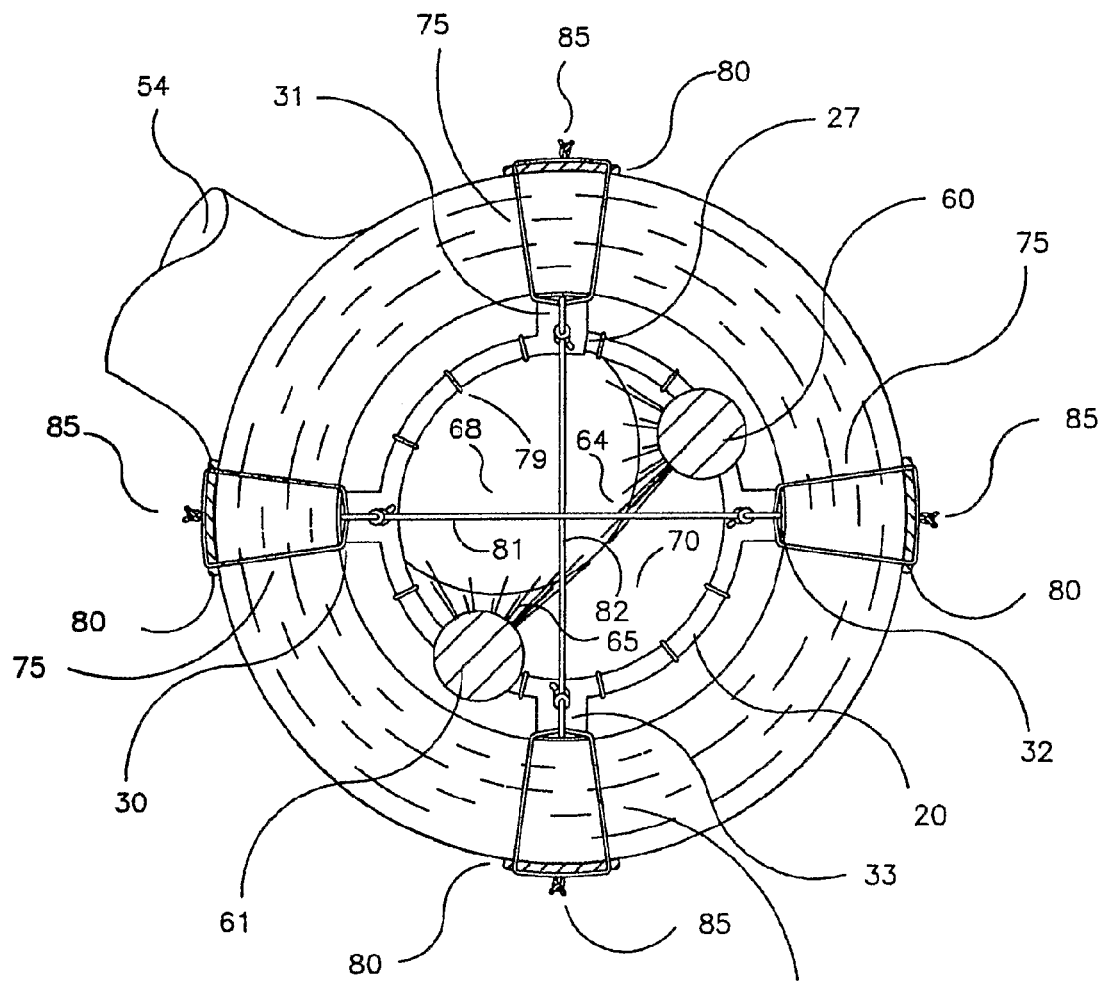
FIG. 8 is a cross-sectional view of the left ventricle view of the heart at initial systole taken along line EE of FIG. 7.

FIG. 7 shows a cross-sectional view of the left ventricle with the first embodiment of the invention implanted, and FIG. 8 shows a cross-sectional view of the left ventricle, taken along line EE of FIG. 7. Both FIG. 7 and FIG. 8 show the left ventricle in the early systolic phase, with the mitral valve 51 closed and the aortic valve 50 open. FIG. 7 shows the left myocardium 52, aortic outflow tract 54, and the left atrium 55, left ventricular apex 56, and the aortic valve 50. The mitral valve mechanism consists of the two papillary muscles 60, 61, the two sets of chordae tendineae 64, 65 and the anterior 68 and posterior 70 leaflets of the mitral valve.

The bistable cage 10 is secured to an inner circumferential periphery 13 of the ventricle by means of suitable sutures 75, passed through the myocardium 52 and which may be supported by external epicardial pledget members 80 or other suitable reinforcing structures. For simplicity, the specification mentions only pledgets specifically. The sutures are conveniently terminated by epicardial knots 85 placed over the epicardial pledgets 80. Top circumferential band 20 is retained closed by suture 84 terminated by knot 89, and secured to the mitral annulus by a series of sutures 74, reinforced with pledgets 73 and terminated in knots 72. Bottom circumferential band 15 is secured to the myocardium near its apex by suitable sutures 79, passed through the myocardium 52 and supported by external epicardial pledget members 86 and secured by knots 87. Optional flexible cables 81, 82 terminated with loops 83 and knots 88 are retained firmly against members 30, 32 and 31, 33 respectively by implanting sutures 75. Optional flexible cables 81, 82 serve to restrict the maximum diameter of the device, and hence limit the end diastolic diameter of the heart. Cables 81, 82 may be of expanded Poly Tetra Fluro-ethylene (PTFE, sold commercially as GORE-TEX®), a material that has been used successfully to replace chordae tendineae in mitral valve repair operations.

FIG. 9 is a cross-sectional view of the left ventricle, and FIG. 10 is a cross-sectional view of the left ventricle, taken along line FF of FIG. 9. Both FIG. 9 and FIG. 10 show the left ventricle in the early diastolic phase, with the mitral valve 51 open and the aortic valve 50 closed. The bistable cage 10 is in its second bistable state or the contracted stable state as shown in FIGS. 4 and 5.

Figure 11:
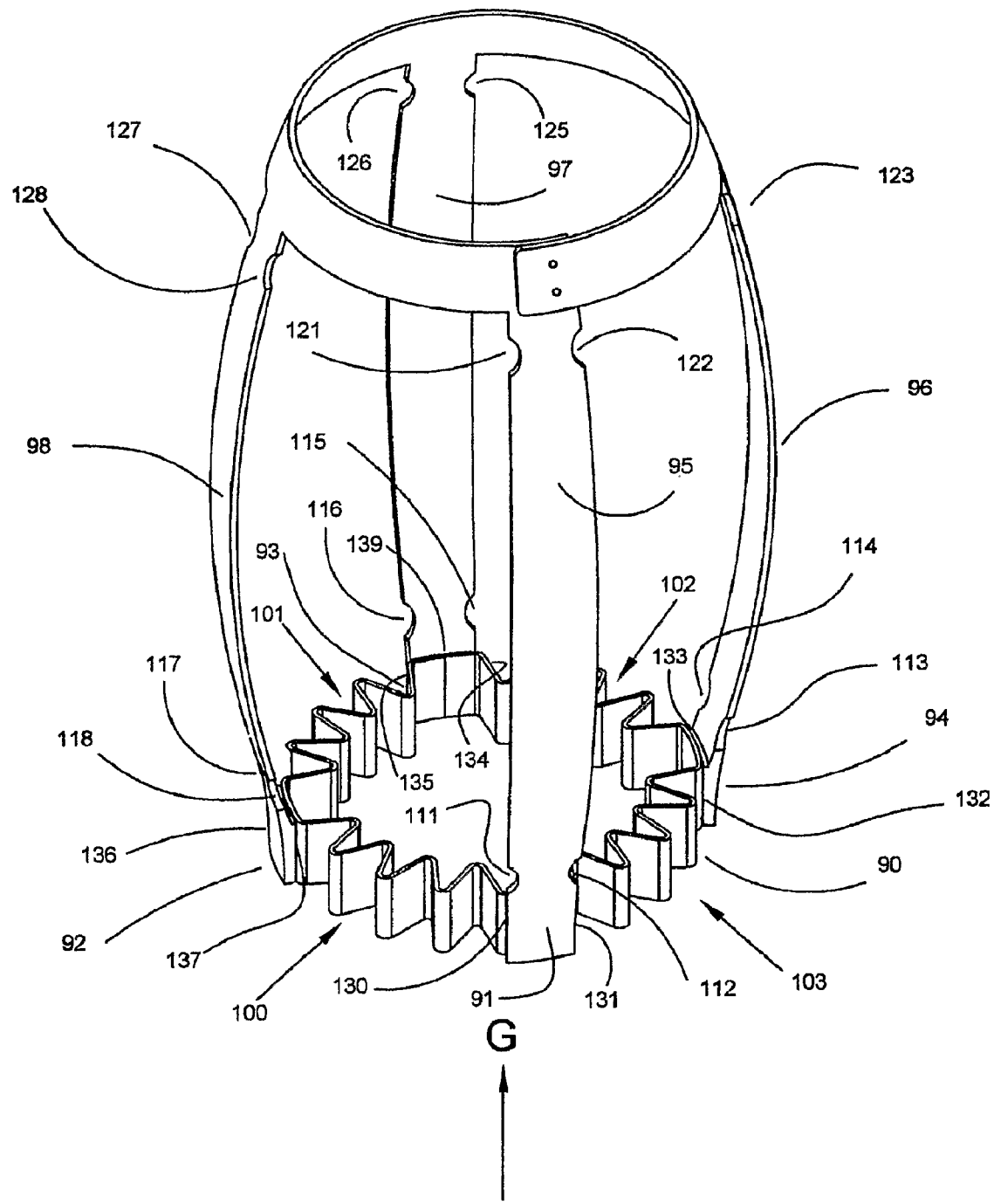
FIG. 11 is an isometric view of an alternative embodiment of the bistable element of FIG. 1 in a first bistable expanded condition.
Figure 12:
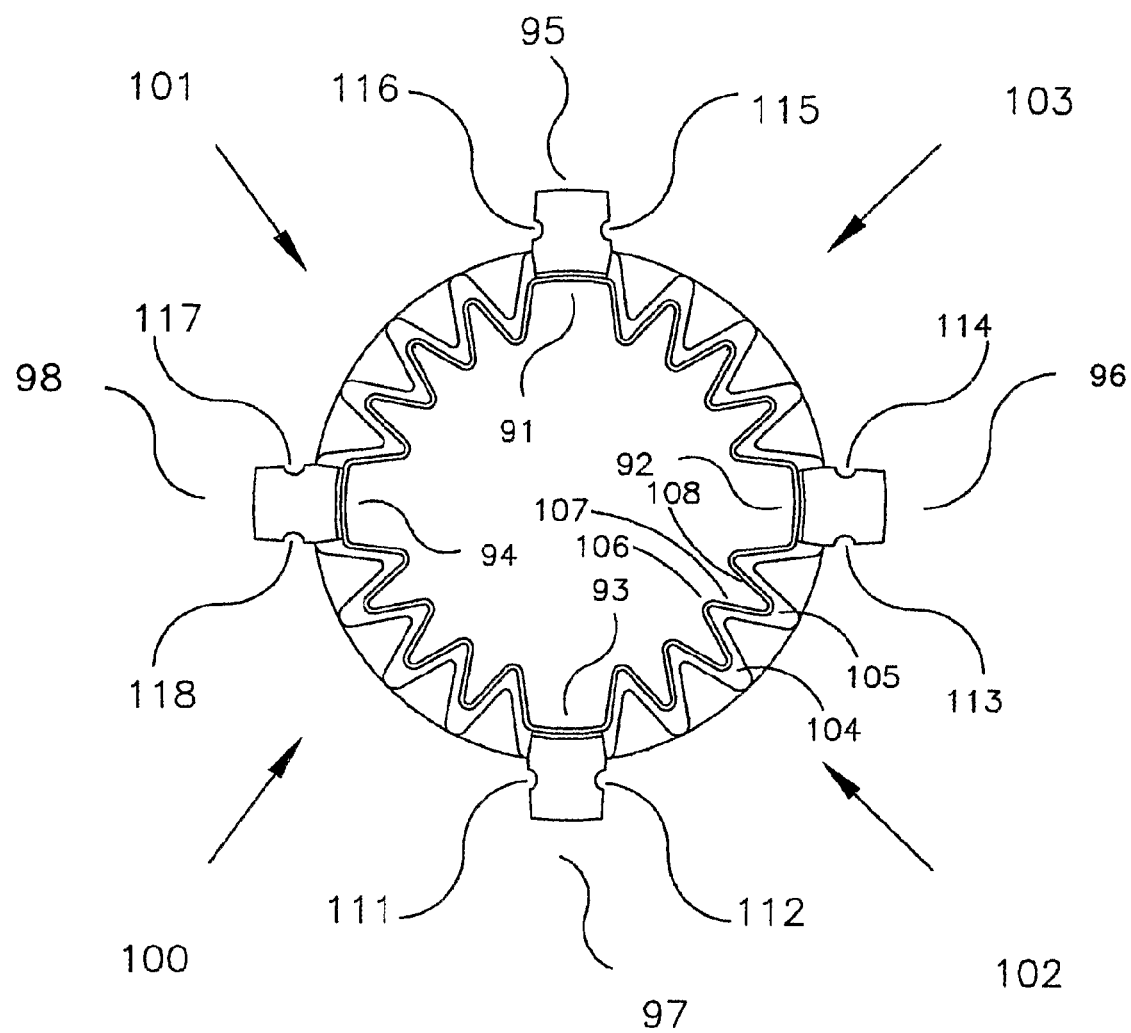
FIG. 12 is a plan view of the alternative embodiment of the bistable element of FIG. 1 taken in the direction of arrow G in FIG. 11.

FIGS. 11 and 12 show alternative embodiments of the first embodiment shown in FIG. 1, in which the inextensible bottom circumferential band 15 of FIG. 1 has been replaced by a convoluted member 90 that acts as a spring that allows its effective diameter to expand and contract in response to applied forces. The convoluted member 90 is composed of four plain segments 91, 92, 93, 94 located at the lower end of the longitudinal members 95, 96, 97, 98. Between plain segments 91 and 92 lies convoluted segment 100, and likewise between plain segments 92 and 93 lies convoluted segment 101 and between plain segments 93 and 94 lies convoluted segment 102, and between plain segments 94 and 91 lies convoluted segment 103. Each convoluted segment contains multiple convex portions illustrated by 104, 105 multiple concave portions illustrated by 106 joined by multiple linear sections illustrated by 107, 108. FIG. 11 shows three convex sections, four concave sections joined by six linear sections. However, those skilled in the art will understand that more or fewer convolutions could be used with effect. The illustration in FIG. 11 is not meant to limit the number of convolutions used.

In another alternative of the embodiment as depicted in FIGS. 11 and 12, one or more of the longitudinal members 95, 96, 97, 98 comprise recesses located near to the upper and lower ends of the longitudinal members. The recesses 111, 112, 113, 114, 115, 116, 117, 118 form hour-glass sections and are located near the lower end of the longitudinal members, and recesses 121, 122, 123, 124, (124 is hidden from view) 125, 126, 127 and 128 also form hour-glass sections and are located near the upper ends of longitudinal members 95, 96, 97 98. The hour-glass sections, being areas of increased flexibility, cause the longitudinal member to flex from one stable position to a second stable position at these predetermined areas. Although one hour-glass section is shown near each end of the longitudinal members, those skilled in the art will recognize that more or less than two recesses may be placed at various locations along a longitudinal band, depending upon the material characteristics and dimensions (length, width and thickness) of the longitudinal band. The longitudinal bands 95, 96, 97, 98 may be unitized with the convoluted lower member 90, or for ease of manufacture may be joined to member 90 by rivets or using an adhesive, or preferably by electron beam or laser welding. As shown in FIG. 11 and FIG. 12, the welds are located at 130, 131, 132, 133, 134, 135, 136, and 137. Also for convenience of manufacture lower member 90 may be likewise made from flat sheet material and joined by electron beam or laser welding along a line 139, shown in FIG. 11.

In the embodiments shown in FIGS. 1-11, the bands are arranged in an elliptically shaped cage to approximate the shape of the normal ventricle (left or right). The cage is comprised of circumferential as well longitudinal bands that during implantation are anchored to the myocardial wall at specified sites, by, for example, surgical sutures. The act of suturing the cage into the ventricle restricts the diastolic chamber size thereby reducing initial systolic myocardial wall stress.

As discussed above, the longitudinal bands of the cage are formed so as to be able to shift between contracted and expanded stable states, thus making the cage bistable. The bands, which are anchored to the myocardium, are sensitive to the lateral forces of a contracting left ventricle during systole, initiating movement in the same direction toward an end desirable diameter. The contracting and, therefore, shortening left ventricle also applies a powerful axial force to the longitudinal axis of the device. These two forces working in concert, generate a lateral displacement of the elements of the device causing the device to spring into the opposite bistable direction, or contracted state, releasing stored energy, and creating a powerful pumping force. The changed resting state of the longitudinal bands in the contracted state are sensitive to the lateral forces generated by the diastolic ventricular relaxation, initiating movement of the longitudinal elements in the same direction toward the opposite bistable state. The relaxing and elongating ventricle facilitates the movement of the longitudinal element in the direction of toward the expanded bistable state. Once displaced a select amount, the bistable element springs toward the expanded state. The corresponding release of stored energy augments the ventricular wall expansion of diastole and thereby creates a "sucking" force to enhance left ventricular filling and restore optimal diastolic function. Furthermore, the longitudinal structure of the device applies a restrictive force to fix the end-diastolic dimensions of the left ventricle to a more optimal size, shape and volume and, thereby, reduces myocardial wall stress during early systole. Optional transverse cables with loops retained firmly against opposing longitudinal bands restrict end diastolic diameter of the heart.

Although not illustrated, the bistable cage could be enclosed in a biocompatible sheath or coating as discussed with respect to the second embodiment below.

In restoring an optimal mechanically efficient elliptical cardiac shape, the device allow an effective range of sarcomere length change to maximize resting and active tension states for optimization of stroke volume throughout a large range of after load. Furthermore, in addition to fixing diastolic and systolic volumes, the devices assist the active phases of both diastole and systole by augmenting the active contractile force of diseased myocardium in systole and the relaxation of myocardium in diastole. In systole, maximum systolic emptying is increased and, in diastole, the devices provide an augmented restoring force that provides "suction" in early diastole to enhance early ventricular filling.

Figure 13:
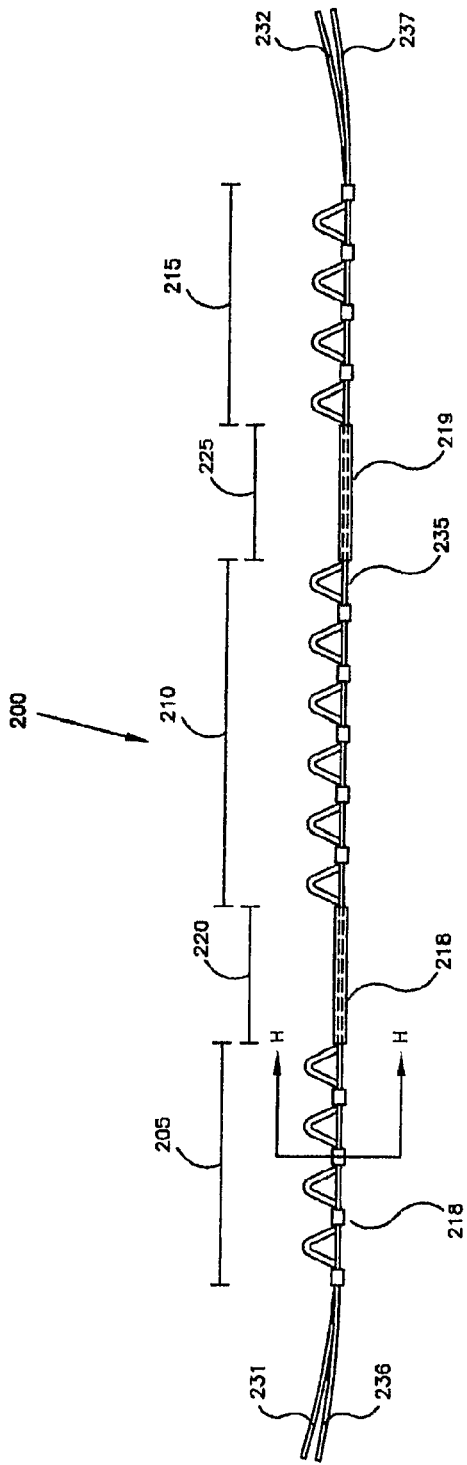
FIG. 13 is a side elevation view of a second embodiment of an apparatus implantable in a heart ventricle for providing mechanical assist comprising an implantable spring band.
Figure 14:
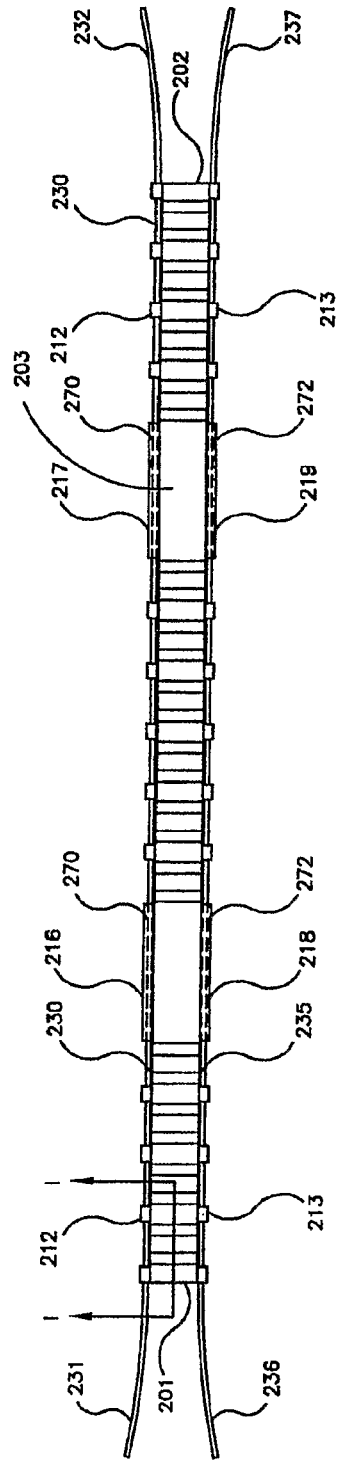
FIG. 14 is a plan view of the implantable spring band of FIG. 13.

A second embodiment of the apparatus implantable in a heart ventricle for providing mechanical assist to the operation of the ventricle is in the form of an implantable spring frame or band as shown in FIGS. 13 and 14. The implantable spring band 200, has a first end 201 and a second end 202 and comprises interrupted "concertina" type spring member sections 205, 210, and 215 operatively associated axially with the band, separated by planar sections 220, 225. The inner spring member 240 of the band is encased in a biocompatible sheath 203. In the embodiment disclosed herein a "sheath" is described. It should be appreciated by one of skill in the art that other forms of coating with biocompatible materials may be preferred for certain designs and applications.

As shown in FIG. 14 longitudinal ligatures 230, 235 are partially enclosed in multiple short tubes 212 situated on a first side and forming part of the sidewalls of sheath 203, and other multiple short tubes 213 situated on a second side and forming part of the sidewalls of sheath 203. Additionally, two pairs of long tubes, 216, 217, 218, 219, also form part of the sidewalls of the sheath. Ligature 230 has a first tail 231 and a second tail 232. Ligature 235 has a first tail 236 and a second tail 237.

FIG. 15 shows an enlarged cross-sectional view through sheath 203 taken along line HH of FIG. 13. FIG. 16 shows an enlarged partial cross-sectional view through sheath 203 taken along line II of FIG. 14.

Referring to FIG. 15, spring band 200 includes inner spring member 240 which is shown enclosed within biocompatible sheath 203 that has an upper wall 263 and a lower wall 265 and is bounded by integral tubes 212, 213 in the section shown in FIG. 15. Tubes 212, 213, have lumens 270, 272 respectively, through which ligatures 230, 235 are free to pass.

The inner spring member 240, shown in side elevation in FIG. 17 and in plan view in FIG. 18, has a first end 241 and a second end 242. Spring member 240, has concertina type spring sections 205a, 210a, 215a separated by planar sections 220a, 225a. These sections correspond to similar sections in FIGS. 13 and 14, e.g. the section of the spring member designated as 205a in FIG. 17 is contained within section 205 of the device shown in FIG. 13. Likewise other similarly designated sections correspond accordingly. FIG. 19 and FIG. 20 show respectively greatly enlarged part side and plan elevations of spring section 205a shown in FIGS. 17 and 18, and a small portion of planar section 220a, likewise shown in FIGS. 17 and 18.

Referring now to FIGS. 19 and 20, which are greatly enlarged side and plan elevation views of section 205a of FIGS. 17 and 18, inner spring member 240 has a short planar portion 253 adjacent to first end 241, rounded root 255, flank 260, and rounded crest 265 that are linearly arrayed to form successive portions of the concertina springs shown in FIGS. 17 and 18.

FIG. 21 shows a plan view of the extruded length of extruded flexible member 250 used to manufacture the flexible biocompatible sheath, cut to the required length having first end 251 and second end 252. The sheath is preferably made from a low thrombogenic, low tissue in-growth material such as extruded and expanded Poly Tetra Fluro-ethylene (PTFE), sold commercially as TEFLON®. Alternatively, a medical grade of woven, knitted or braided Polyester cloth could be used.

FIG. 22 shows an enlarged cross-sectional view taken along line JJ of FIG. 21. Central cavity 260, which contains spring member 240 is bounded by upper wall 262 having upper face 263, lower wall 264 having lower face 267 and integral tubes 266 and 268. Tube 266 has lumen 270 and tube 268 has lumen 272. Excess material in tubes 266, 268 is later cut away (as indicated by cross-hatched section 271, 273 in FIG. 21 delineated in part by the dashed lines 274, 275 that emanate from the final form shown in FIG. 24) to form the final sheath 203. The other delineations of the cut-outs are shown in FIG. 23, which shows an enlarged cross-sectional view taken along line KK of FIG. 24. The view shows that sections 266, 268 have been partially cut away leaving vertical faces 277, 277a, 277b and 278, 278a, 278b (FIG. 24) respectively. Only one pair of cut-out delineations are indicated on FIG. 21 but it should be clear to one skilled in the art that the cut-out procedure is repeated as appropriate along the entire length of the sheath.

The inner spring member 200 is preferably made from Nickel Titanium (Ni Ti) alloy, MP35N alloy, or a similar "memory metal" alloy or metal, having a significant fatigue life. As the average age of the patient expected to be approximately in the range of 60-80 years old with a probable mean age of 70 years old, with a natural life expectancy of another 10 years, and on average, the human heart beats approximately 45 million times a year, the optimum fatigue life of the device is preferably at least 450 million cycles.

The spring material is memory may set to its final form shown in FIG. 17 at below operating room temperature (typically 65° F.). Following suitable heat treatment of the material at sub-operating room temperatures the spring may be straightened (or near straightened) and the extruded and trimmed PTFE sheath 203 shown in FIG. 23 slid over the then straight metal strip. On re-warming to a temperature above its transition temperature the flat spring reconfigures to its pre-determined semi-convoluted form shown in FIG. 17 and the device takes on the form shown in FIG. 13. The two side ligatures 230, 235, preferably also of expanded PTFE, are then passed though all side tubes and the end trimmed to produce convenient suture tails 231, 232, 236, 237. Finally walls 262 and 264 at end 252 and 254 are pulled and sewn to complete the device.

The thickness of the inner spring member 240 may be in the range 0.25 mm to 1.0 mm. A thickness of 0.5 mm is believed suitable for some applications. The width of the spring may be in the range 3 mm-20 mm, with a width of 8 mm believed suitable for some applications. The concertina spring has convex radii 255 of approximately 1.5 mm and concave radii 265, of approximately 1 mm, although, clearly the radii may be varied, especially depending upon the thickness of the spring material and the Young's Modulus of the spring material, which is preferably of a biocompatible nature, with a long fatigue life, formed into a concertina shaped spring, encapsulated within a suitable sheath 203.

The implantable spring band is implanted in the left ventricle, adjacent to the endocardium and proximal to the papillary muscles (preferably just above, or alternatively just below), via an incision through the left ventricle wall, and implanted, in conjunction, if necessary, with appropriate left ventricular reduction.

Various implantable spring band lengths may be made available. The surgeon can select, either preoperatively, or during surgery, the most appropriate overall length of the device. Factors influencing selection include the patient's body surface area, weight and sex, and the degree of left modeling required to achieve near left ventricular normality.

During ventricular systole the spring becomes compressed, and during diastole the spring applies an outwards radial force on the ventricular wall that mechanically assists in moving the ventricle toward an end diastole diameter and thus aids in diastolic filling. Alternatively, the spring band could be sized to be relaxed during end systole and then stretched during diastole to provide assist during systole.

Figure 25:
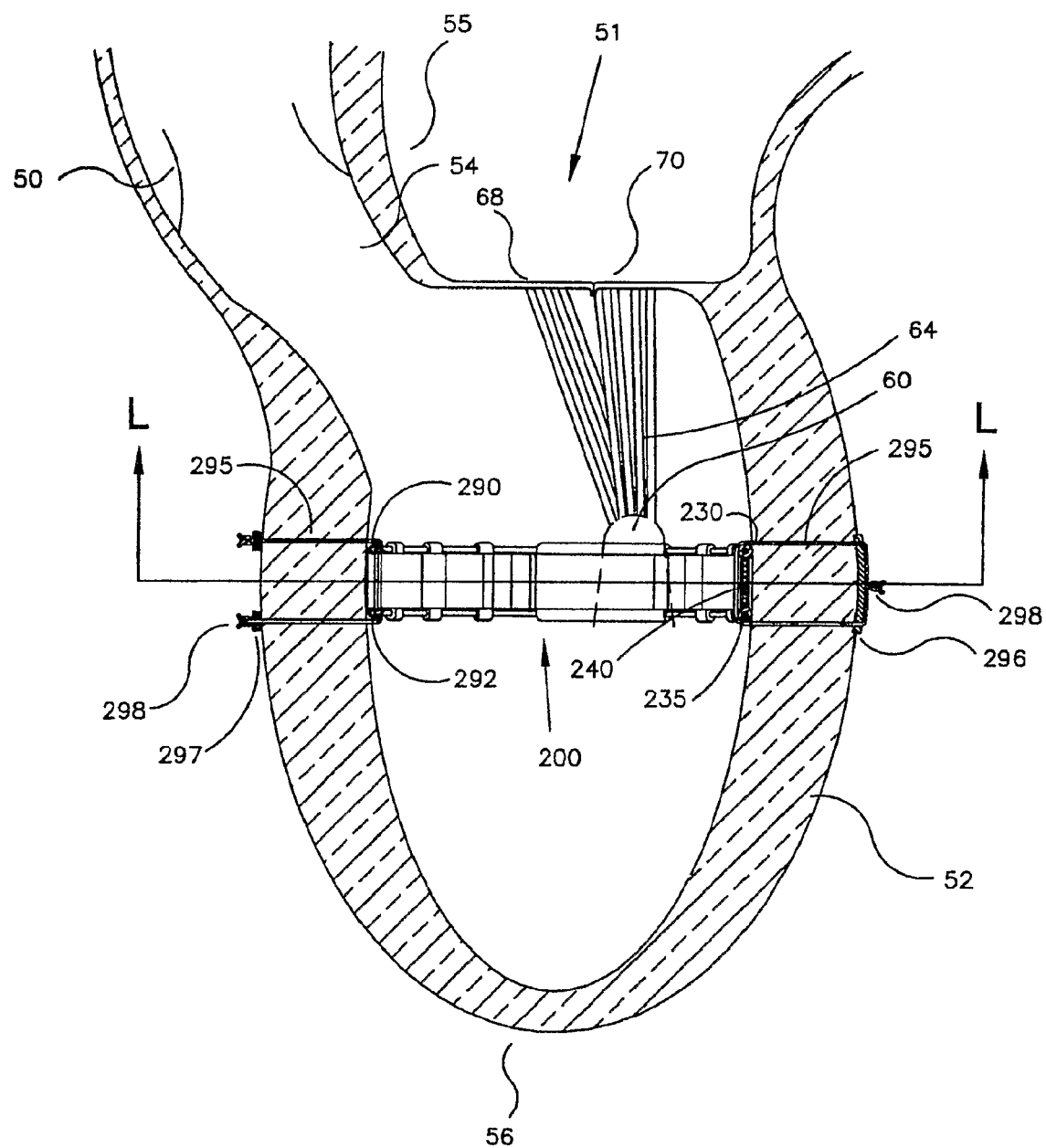
FIG. 25 is a long axis cross-section through a left ventricle of a heart with the implantable spring device implanted.
Figure 26:
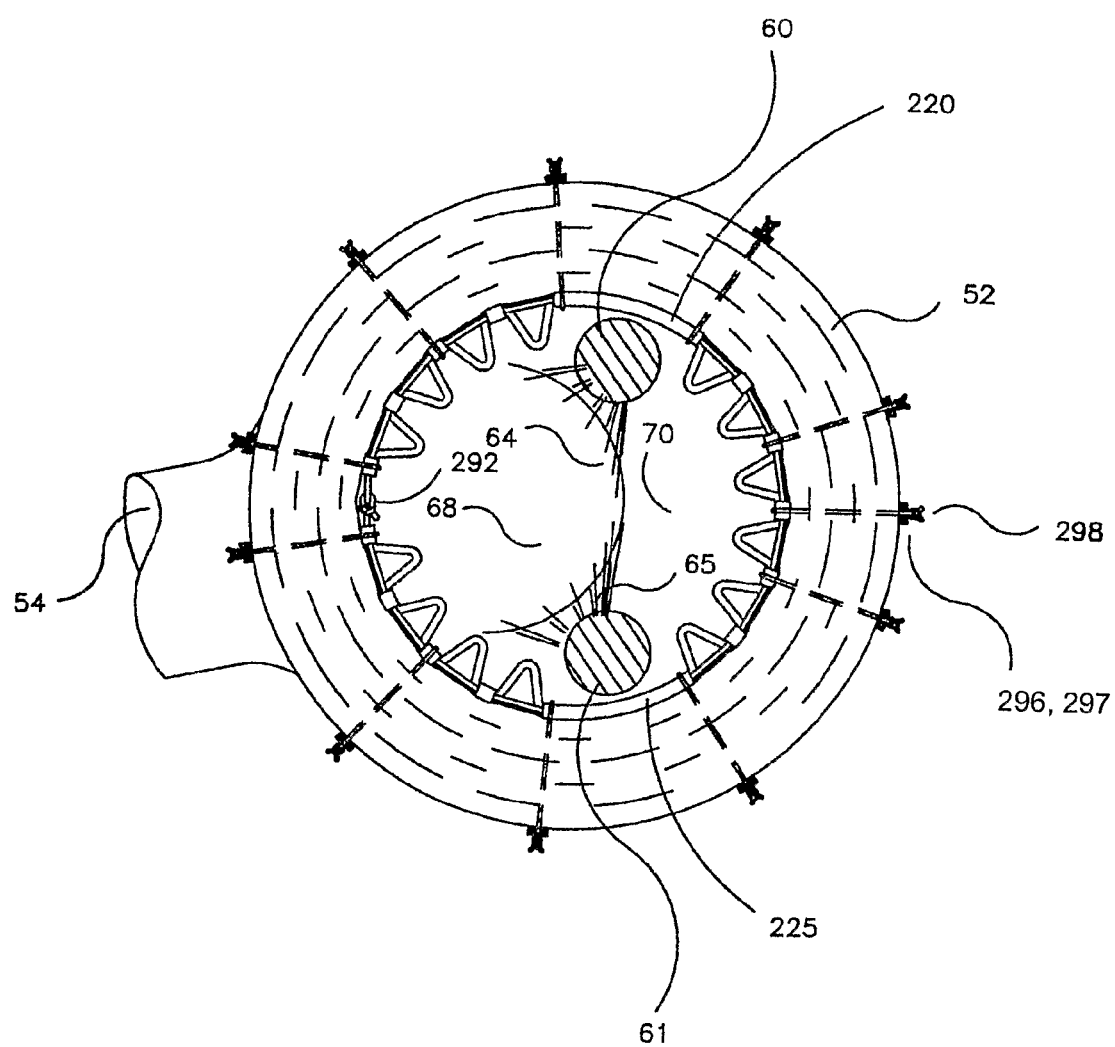
FIG. 26 is a cross-sectional view of the left ventricle of the heart taken along line LL of FIG. 25 with the implantable spring device implanted.

Referring now to FIGS. 25 and 26, FIG. 25 shows a sections through the long axis of the left ventricle (the right ventricle is not shown) with the implantable spring bands shown in FIGS. 13 and 14 implanted. FIG. 26 shows a cross-sectional view of the left ventricle taken along line LL of FIG. 25. During implanting, the device 200 is passed behind the chordae tendineae, the two ends 201, 202 are bought together and the tails 231, 232 of ligature 230 are tied, likewise the tails 235, 236 together to form knots forming knots 290, 292, the device forming a loop or a near circular "concertina" type spring as shown in FIG. 25. The device is then rotated about the long axis of the left ventricle so that the plane sections 220, 225 lie adjacent to the papillary muscles in the left ventricle. A series of sutures 295 are passed through the wall of the left ventricle to firmly attach the device to the left myocardium about the circumferential inner periphery of the ventricle. The sutures are buttressed on the epicardium by a series of bridged pledgets 296 or single pledgets 297, the sutures being terminated in knots 298. The myocardial incision is then closed, and the operation completed.

The circumferential ligatures 230, 235, preferably of a low thrombogenic, strong material such as expanded PTFE or braided polyester, positioned on one or preferably both sides of the spring member, and the individual end of each ligature are tied to its other end at implantation, to limit the diameter of the implanted device, and hence the inner maximum diameter (and therefore peak myocardial stress) of the left ventricle.

Figure 27:
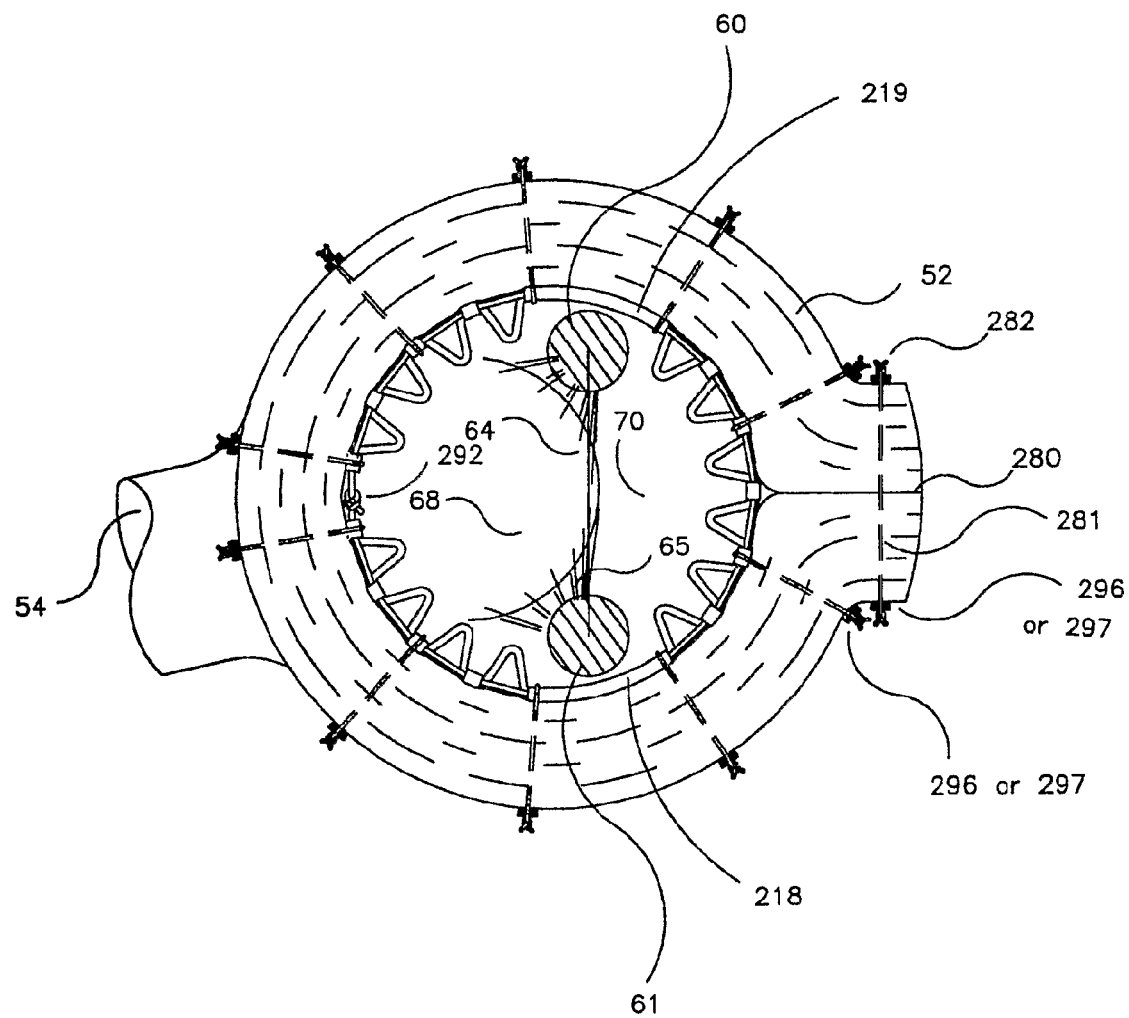
FIG. 27 is a cross-sectional view of the left ventricle of the heart taken along line LL of FIG. 25 with the implantable spring device implanted, but where surgical ventricular reduction has been used.

FIG. 27 shows a transverse cross-sectional view of the left ventricle of the heart (similar to that taken along line LL of FIG. 25) with the spring member device 200 implanted, but where surgical ventricular reduction has been carried out. A section of the left ventricle has been removed, the excised edges of the endocardial wall have been bought together to form junction 280, which are retained by the securing sutures illustrated by 281 terminating with suitable pledgets such as 296, 297 and knots 282. The position of the ventricular incision is illustrative only, the actual location depends on the pathology of the patient and the choice of surgical repair techniques is at the discretion of the surgeon.

Figure 28:
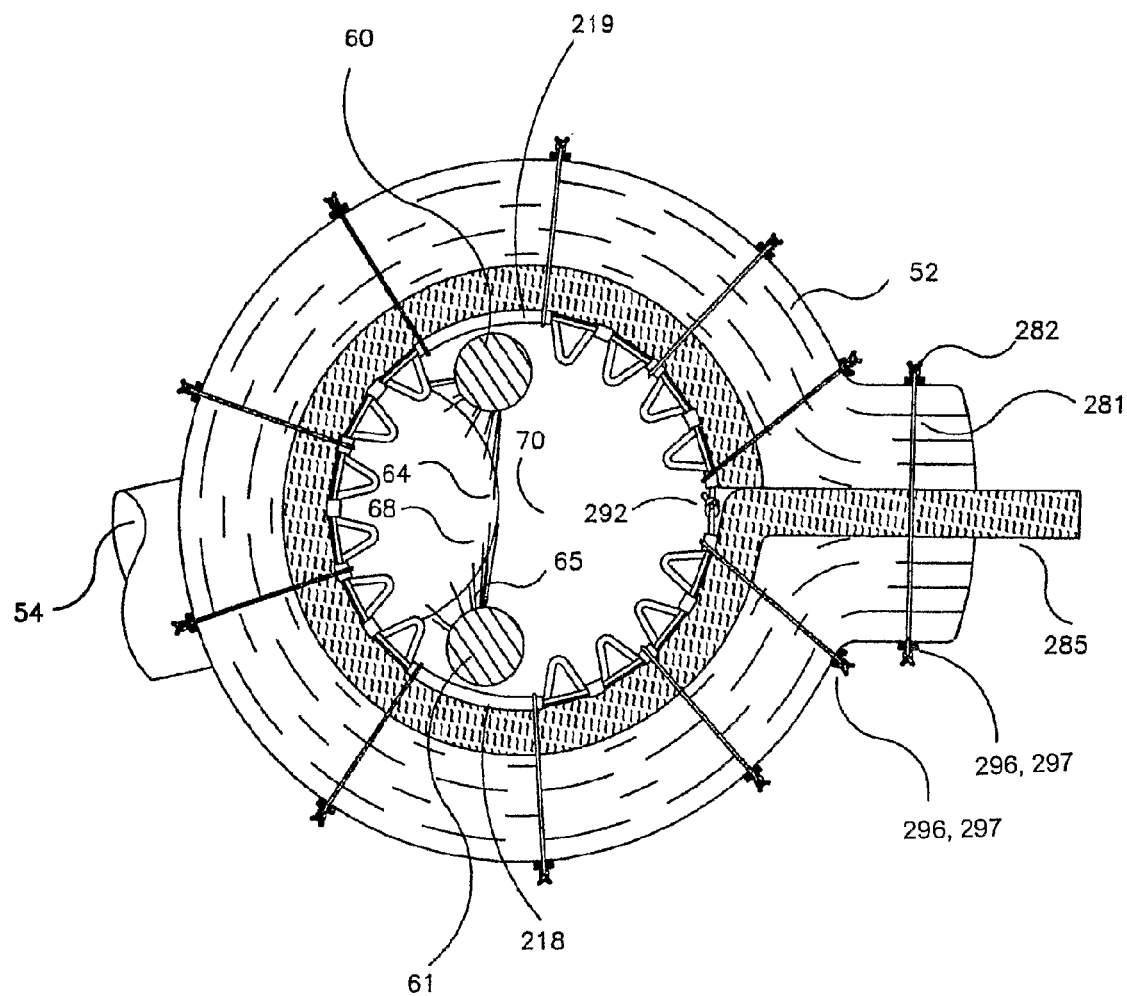
FIG. 28 is a cross-sectional view of the left ventricle of the heart taken along line LL of FIG. 25 with the implantable spring device implanted, but where surgical ventricular reduction has been used and a portion of the trained latissimus dorsae muscle has been wrapped around the device within the heart.

FIG. 28 shows a transverse cross-sectional view of the left ventricle of the heart (similar to that taken along line LL of FIG. 25) with the implantable spring band 200 implanted, but where surgical ventricular reduction has been made and a portion of the trained latissimus dorsae muscle 285 has been wrapped around the spring band within the heart. Pacing electrodes (not shown) placed on the latissimus dorsae muscle and connected to a pacemaker cause the muscle to contract synchronously with that of the myocardium.

Figure 29:
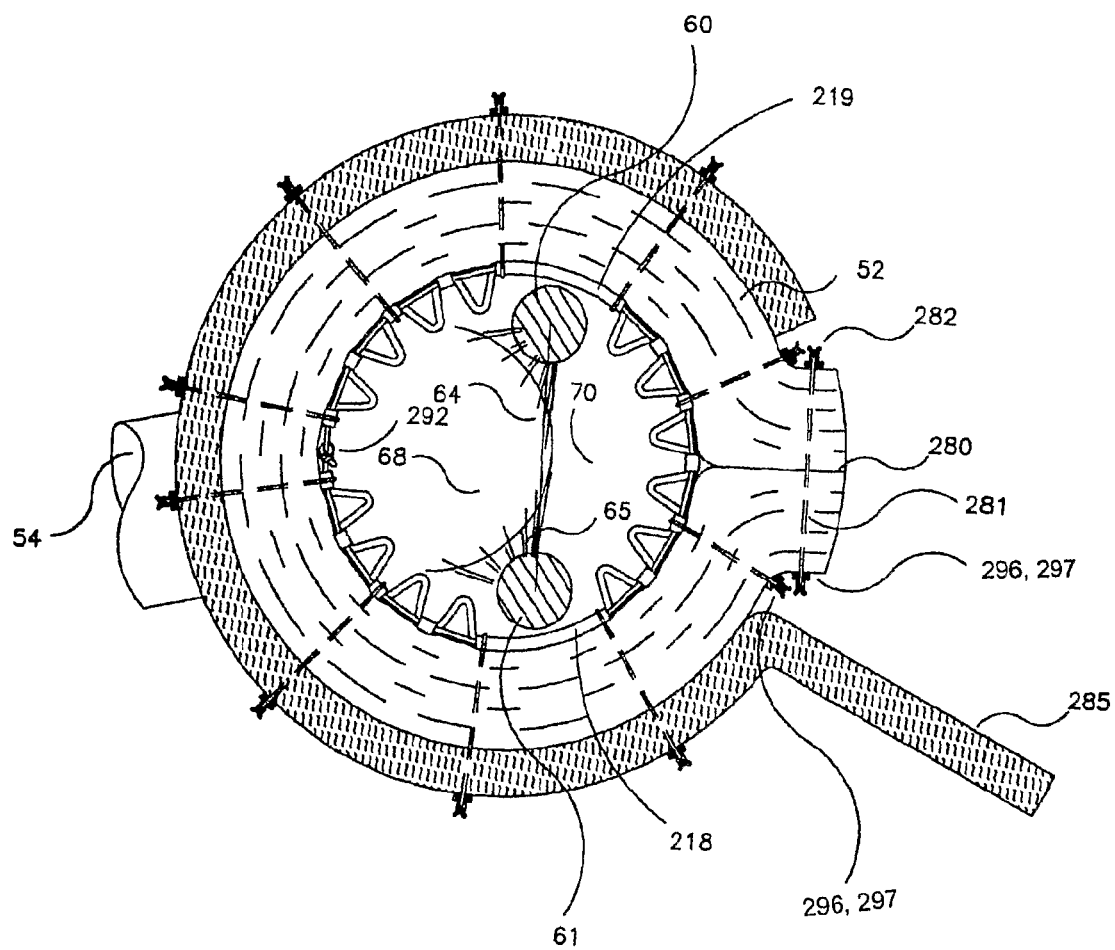
FIG. 29 is a cross-sectional view of the left ventricle of the heart taken along line LL of FIG. 25 with the implantable spring band implanted, but where surgical ventricular reduction has been used and a portion of the trained latissimus dorsae muscle has been wrapped around outside of the left ventricle of the heart.

FIG. 29 shows a cross-sectional view of the left ventricle of the heart taken along line LL of FIG. 25 with the spring band implanted, but where surgical ventricular reduction has been made and a portion of the trained latissimus dorsae muscle 285 has been wrapped around outside of the left ventricle of the heart. Pacing electrodes (not shown) place on the latissimus dorsae muscle and connected to a pacemaker cause the muscle to contract synchronously with that of the myocardium.

FIG. 30 shows a plan elevation of an additional embodiment 300 of the spring band 200 previously described, but that incorporates a sub-annular mitral annuloplasty ring 304, that is attached to the planar sections 320, 325 by struts 306, 307. FIG. 30 shows the spring member/annuloplasty device in its final circular form, where the four suture tails 331, 332 and 336, 337 have been tied to form knots 390, 392 (shown later in FIG. 37).

Figures 33, 34:
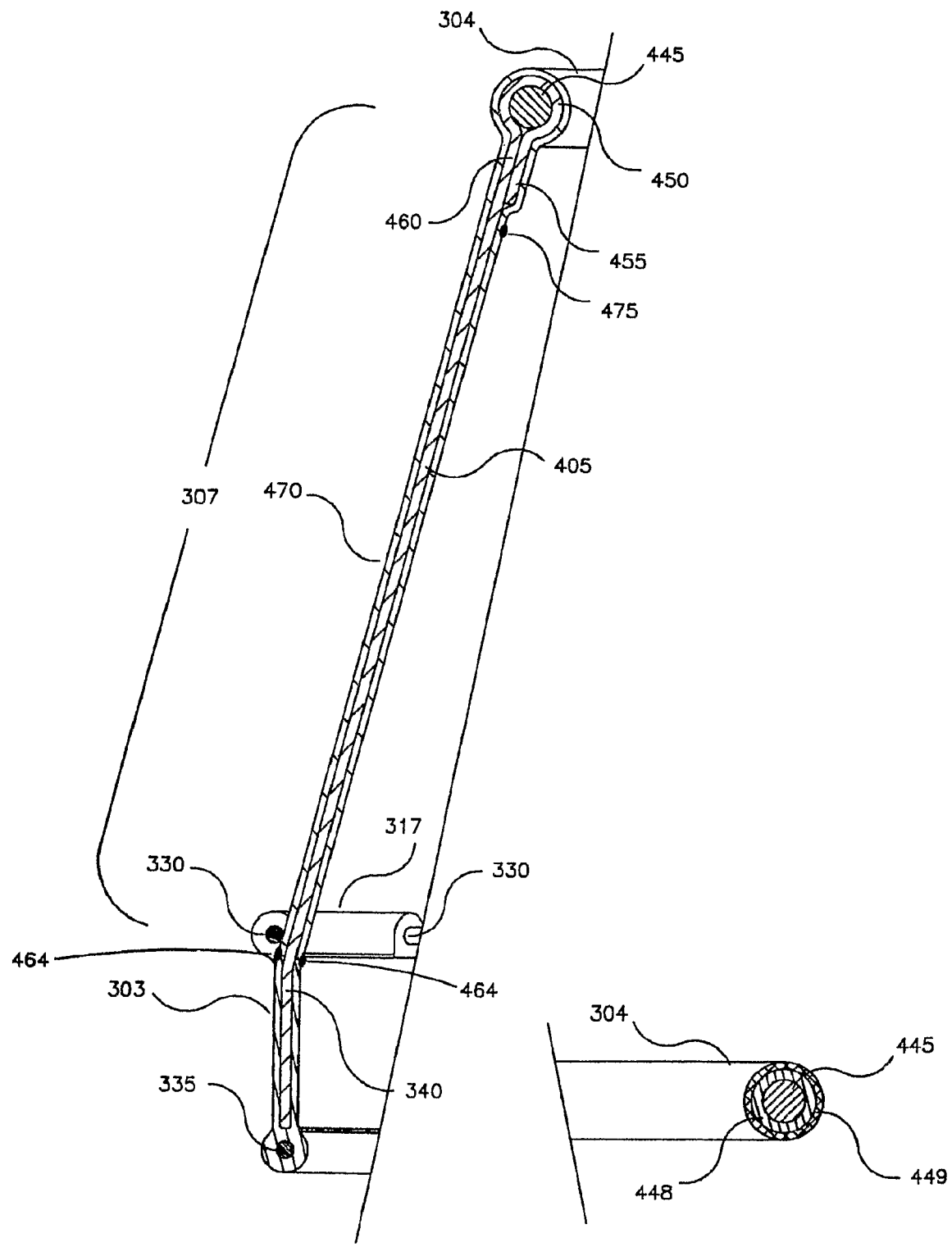
FIG. 33 is an enlarged part cross-sectional view a portion of the alternative embodiment of the implantable spring band taken along line OO of FIG. 30.
FIG. 34 is an enlarged part cross-sectional view of a portion of the alternative embodiment of the implantable spring band taken along line PP of FIG. 30.

FIG. 31 shows a side elevation of the spring band/annuloplasty device taken in the direction of arrow M in FIG. 30. FIG. 32 shows a side elevation of the spring member/annuloplasty device taken in the direction of arrow N of FIG. 30. FIG. 33 shows an enlarged part side section taken along line OO of FIG. 30. FIG. 34 shows an enlarged part side section of the annuloplasty ring member 304 taken along line PP of FIG. 30. Strut 307 inner metallic leg member 405 terminates at its upper end with hoop 450 and overlapping length 455.

As shown in FIGS. 30, 31 and 32 longitudinal ligatures 330, 335 are partially enclosed in a series of a multitude of short tubes 312 situated on first side and forming part of the sidewalls of sheath 303, and a second set of short tubes 313 situated on the second side and forming part of the sidewalls of sheath 303. Additionally, two pairs of long tubes, 316, 317, 318, 319, also form part of the sidewalls of the sheath 303. Ligature 330 has a first tail 331 and a second tail 332. Ligature 335 has a first tail 336 and a second tail 337 (not shown).

Inner spring member 340, shown in side elevation in FIG. 35 and in plan view in FIG. 36, has a first end 341 and a second end 342. Inner spring member 340, has concertina type spring sections 305a, 310a, 315a separated by planar sections 320a, 325a. These sections correspond to similar sections in FIG. 30, e.g. the section of the spring member designated as 305a in FIG. 35 is contained within section 305 of the device shown in FIG. 30. Likewise other similarly designated sections correspond accordingly. Referring now to FIG. 35, spring member 340 has a short planar portion 353 adjacent to first end 341, rounded root 355, flank 360, and rounded crest 365 that are linearly arrayed to form successive portions of the concertina springs shown in FIG. 35. Long planar sections 320a, 325a each have leg members 405, 410. Leg members have a tapered length 415, 420, and a short narrow parallel length 425, 430. The leg members are bent at points 435, 440 at an angle of approximately 15°; the actual angle depends upon the relative dimensions of the device, the size of the annuloplasty ring and the axial distance from the mitral annulus and the papillary muscles. The short narrow parallel lengths 425, 430 are formed to produce a retaining hoop 450 with an overlapping section 455. Hoop 450 is formed, as shown in FIG. 35, to closely match that of the annuloplasty ring core 445.

As with the basic spring member device 300, the spring material in the spring member/annuloplasty device is preferably comprised of a high fatigue limit metal alloy, most preferably of super elastic grade of Nickel Titanium alloy (a super-elastic "memory" metal, depending upon its composition and heat treatment conditions) otherwise known as "Nitinol," or a metal or alloy having equivalent properties. The optimum fatigue life of the spring member/annuloplasty device is preferably at least 450 million cycles.

The thickness of the spring in the spring member/annuloplasty device may be in the range 0.25 mm to 1.0 mm in thickness with 0.5 mm believed to be acceptable for some uses. The width of the spring is preferably about 8 mm wide but may be in the range 3 mm-20 mm, with 8 mm with 0.5 mm believed to be acceptable for some uses. The concertina spring has convex radii 355 of approximately 1.5 mm and concave radii 365, of approximately 1 mm, although, clearly the radii may be varied, especially depending upon the thickness of the spring material and the Young's Modulus of the spring material, which is preferably of a biocompatible nature, with a long fatigue life, formed into a concertina shaped spring, encapsulated within a suitable sheath 303. The sheath is preferably made from low thrombogenic, low tissue in-growth material such as extruded and expanded Poly Tetra Fluro-ethylene (PTFE). The device is implanted in the left ventricle, adjacent to the endocardium and proximal to the papillary muscles (preferably just above, or alternatively just below), via an incision through the left ventricle wall, and implanted, in conjunction, if necessary, with appropriate left ventricular reduction.

Various device lengths would be made available. The surgeon would select, either preoperatively, or during surgery, the most appropriate overall length of the device. Factors influencing selection would include the patient's body surface area, weight and sex, and the degree of left modeling required to achieve near left ventricular normality.

The implantable spring with the upper annuloplasty ring retaining ring hoops material may be memory set to the final form shown in FIG. 35 and FIG. 33 at below operating room temperature (typically 65° F.). Following suitable heat treatment of the material at sub-operating room temperatures the spring may be straightened (or near straightened). The annuloplasty ring retaining hoops 450, with overlapping sections 455, are partially distorted just sufficient to allow the annuloplasty ring core 445 to be snapped into position.

The annuloplasty ring 304 is shown as a "C" shaped ring, however those skilled in the art will understand that a semi-circular or semi-elliptical may be used. It is necessary that the ring be open so that the chordae tendineae may be passed through the open section during implantation. The ring is preferably sufficiently strong and rigid to restore the mitral annulus to its pre-diseased size and shape and hence restore the coaptation of the mitral valve leaflets should the annulus have become pathologically distorted, and further to prevent future distortion or enlargement of the mitral annulus. The structural core 445 of the annuloplasty ring 304 may be comprised of a suitable biocompatible material such as ceramic, plastic or metal. Metals such as stainless steel, Titanium or Nickel Titanium alloy (e.g. Nitinol), however, preferably the annuloplasty ring core should be of similar material to the spring member 340 and strut members 405, 410 to avoid galvanic corrosion.

The inner spring member 340 may be covered using a similar sheath to the extruded and trimmed sheath shown previously in FIG. 23. However, because the legs 415, 420 protrude from spring member 340 it is not possible to slide the sheath into place. In one embodiment the sheath is divided into three lengths 466, 467, 468. Firstly, two equal lengths of sheath 466, 467 are pushed, one onto each end section. Secondly, the third length 468 is slit, preferably midway along wall 264 (the wall 264 is shown in FIG. 15), opened out, placed on the mid section of convoluted spring 340, and the cut edges sewn together to form longitudinal seam 460, shown in FIGS. 31 and 32. Sheath member 468 is sewn to sheath member 466 at sheath seam 462, and to sheath member 467 at sheath seam 463 (shown in FIG. 37).

Once the sheath 303 is in place the annuloplasty ring core 455 is snapped into hoops 405 and the device heat treated to a temperature above the material transition temperature. The flat spring reconfigures to its predetermined semi-convoluted form and the hoops 450 firmly grasp the annuloplasty ring core 455. Junction 460 may be fixed by adhesive, welding, silver soldering, riveting or other suitable means.

The struts leg members 405, 410 may be covered with a similar biocompatible covering 470 which is sewn to sheath 303 at leg seams 464 and 465, and having top seams 475 and 476. Annuloplasty ring 304 is shown in cross section in FIG. 34 typically has a rigid central core member 445, that may, optionally have a resilient covering 448 of a suitable biocompatible material such as medical grade silicone rubber and an outer sheath 449 of a suitable biocompatible material such as polyester woven, knitted cloth or braided tube. Finally the two side ligatures 330, 335, preferably also of expanded PTFE, are then threaded through successive short and long tubes to complete the device.

Figure 37:
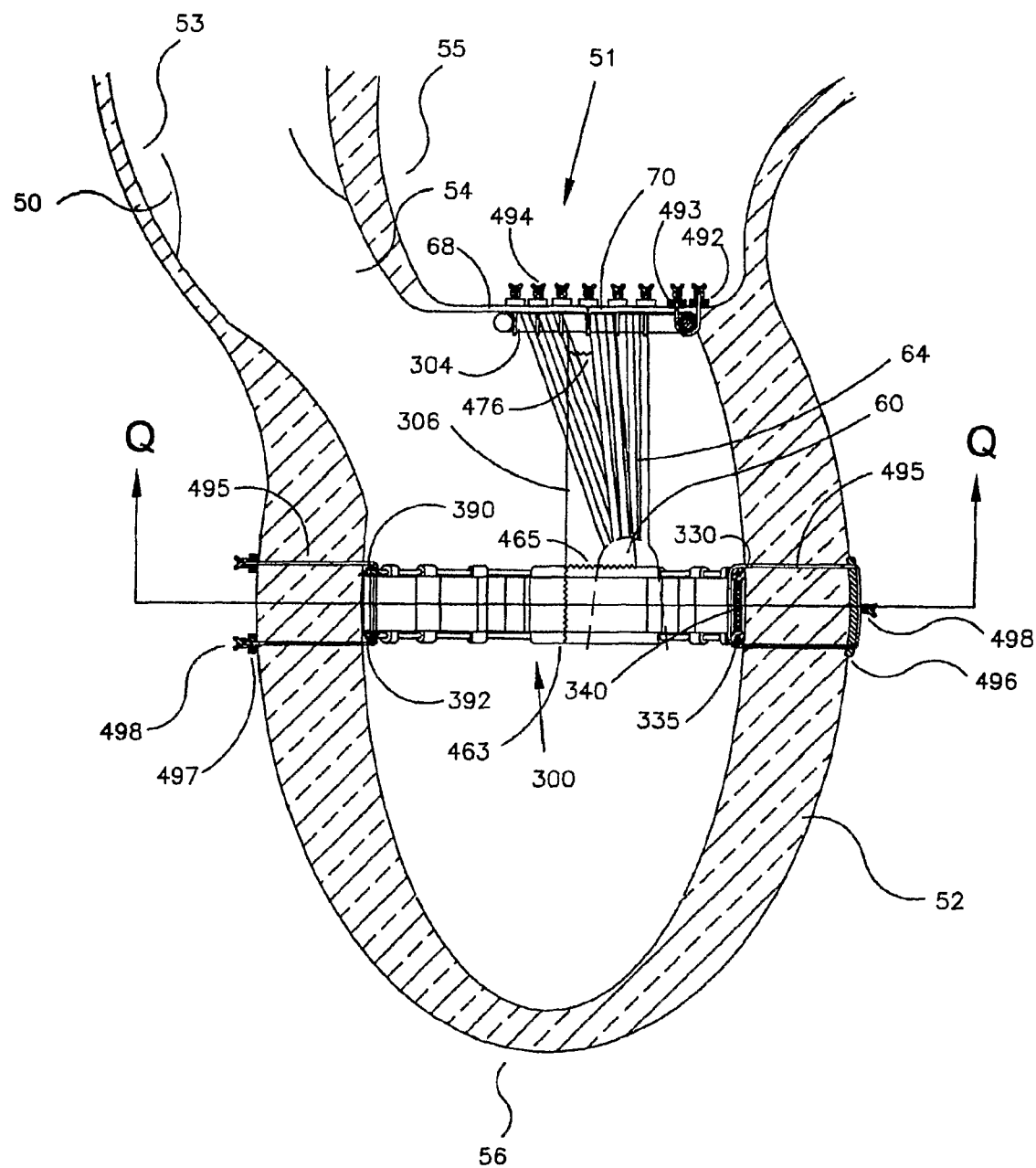
FIG. 37 is a long axis cross-sectional view of the left ventricle of the heart with the alternative embodiment of the implantable spring band incorporating a sub-annular annuloplasty ring implanted.

FIG. 37 shows a cross-section through the left ventricle (the right ventricle is not shown) with the device shown in FIG. 31 implanted. An incision (not shown) is made in the left ventricle and the device inserted. The chordae tendineae are passed through the gap in the "C" shaped mitral annuloplasty ring, the device 300 is passed behind the chordae tendineae, the two ends 301, 302 are brought together and the tails 331, 332 of ligature 330 are tied, likewise the tails 335, 336 together to form knots forming knots 390, 392, the device forming a near circular "concertina" type spring as shown in FIG. 25. The device is then rotated about the long axis of the left ventricle so that the plane sections 316, 317 lie adjacent to the papillary muscles in the left ventricle. A series of annuloplasty sutures 493, with pledgets 492, and secured by knots 494, are passed through the mitral annulus and around the annuloplasty ring 304. FIG. 37 shows annuloplasty sutures placed in the left atrium, however some surgeons might prefer to pass the sutures from the ventricular aspect. Sutures 495 are passed through the wall of the left ventricle to firmly attach the device to the left myocardium. The sutures are buttressed on the epicardium by a series of bridged pledgets 496 or single pledgets 497, the sutures being terminated in knots 498. Other means, such as implanted hooks or other forms of sutures and structures for buttressing the sutures (besides pledgets) are within the scope of the invention. The myocardial incision is then closed, and the operation completed.

Figure 38:
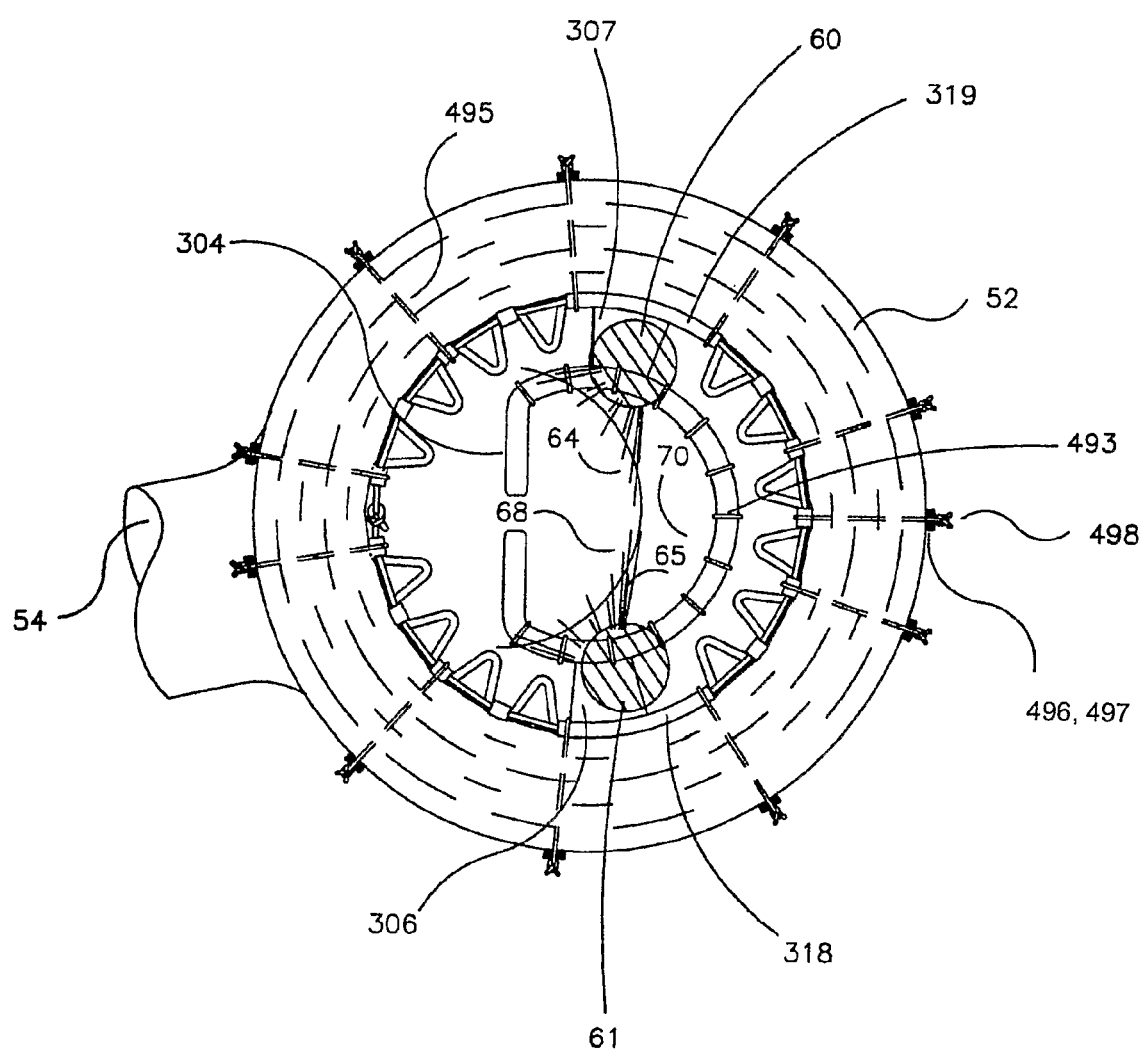
FIG. 38 is a cross-sectional view of the left ventricle of the heart taken along line QQ of FIG. 37.

FIG. 38 shows a cross-sectional view of the left ventricle of the heart taken along line QQ of FIG. 37 with the further alternative embodiment 300 of the invention that incorporates a sub-annular mitral annuloplasty ring 304 implanted.

Figure 39:
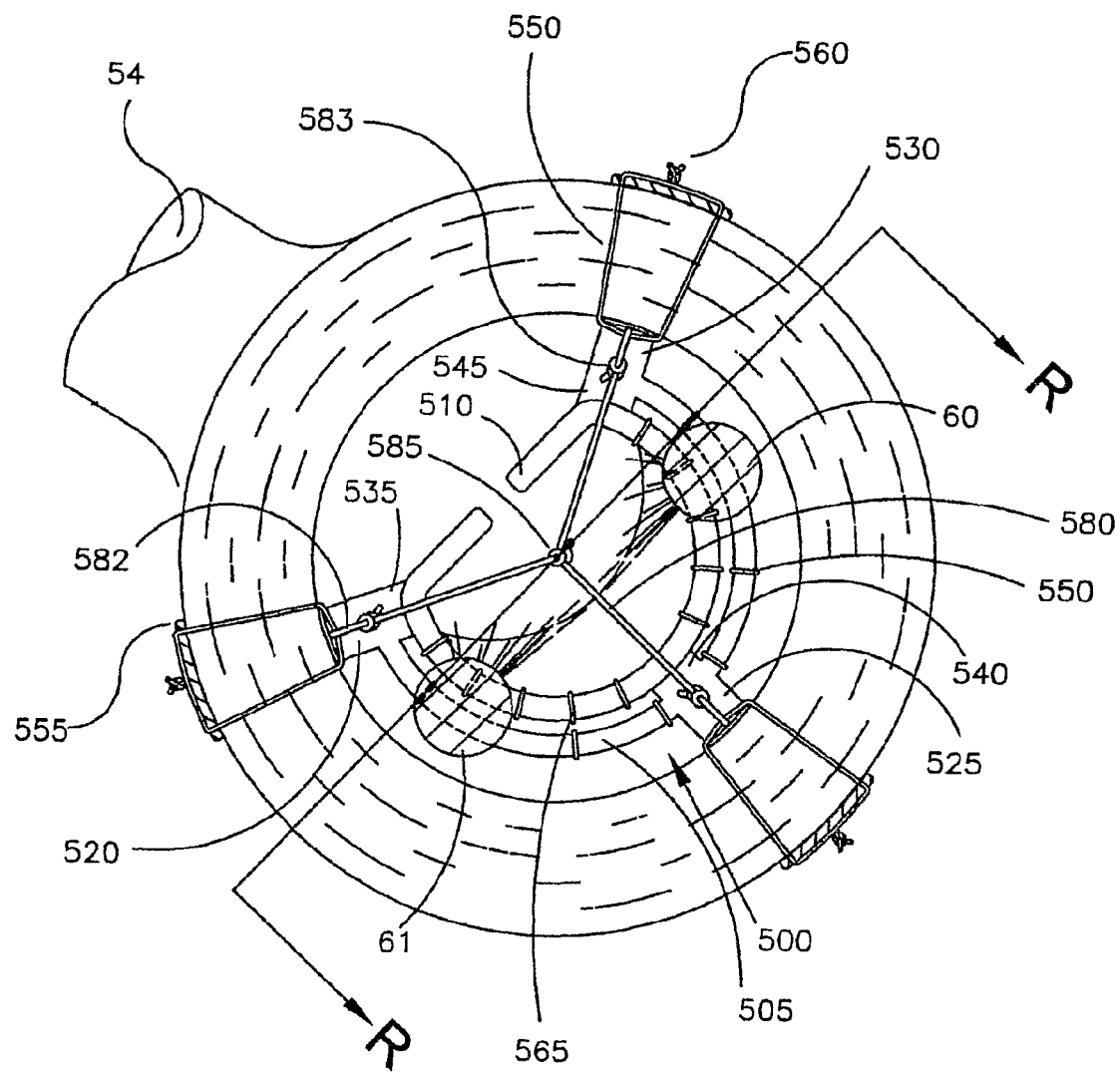
FIG. 39 is a cross-sectional view of the left ventricle of the heart taken along line EE of FIG. 7 with an alternative embodiment of the bistable element shown in FIG. 1 that incorporates a sub-annular mitral annuloplasty ring.

FIG. 39 shows a cross-sectional view of the left ventricle of the heart taken along line EE of FIG. 7 with the further alternative embodiment 500 of the bistable cage 10 that incorporates a sub-annular mitral annuloplasty ring 510 attached to upper hoop 505. FIG. 39 shows the cage having three curved longitudinal strut members 520, 525, 530, but two, four or more struts could be used. Upper hoop 505 is integral to longitudinal struts 520, 525, 530 (as is lower hoop 506 shown later in FIG. 40). Extension members 535, 540, 545, also integral to upper hoop 540, are joined to mitral annuloplasty ring 510. Various method of joining may be employed such as laser or electron beam welding, silver soldering or brazing, or adhesives or by the use of hoops as shown in FIG. 33. A series of sutures 550, with pledgets 555 and secured by knots 560 secure the longitudinal struts to the inner circumferential periphery of the ventricular wall. A second series of annuloplasty sutures 565 are passed through the mitral annulus and around the annuloplasty ring 510. Optional flexible cables 580 are terminated by loops 582 and knots 583. The loops 582 may be retained by implanting sutures 550, or attached by suitable means to the longitudinal struts 520, 525, 530. The cables are joined together approximately in the center of the ventricle by central cable knot 585. The purpose of the optional cables is to limit the end-diastolic diameter of the left ventricle.

Figure 40:
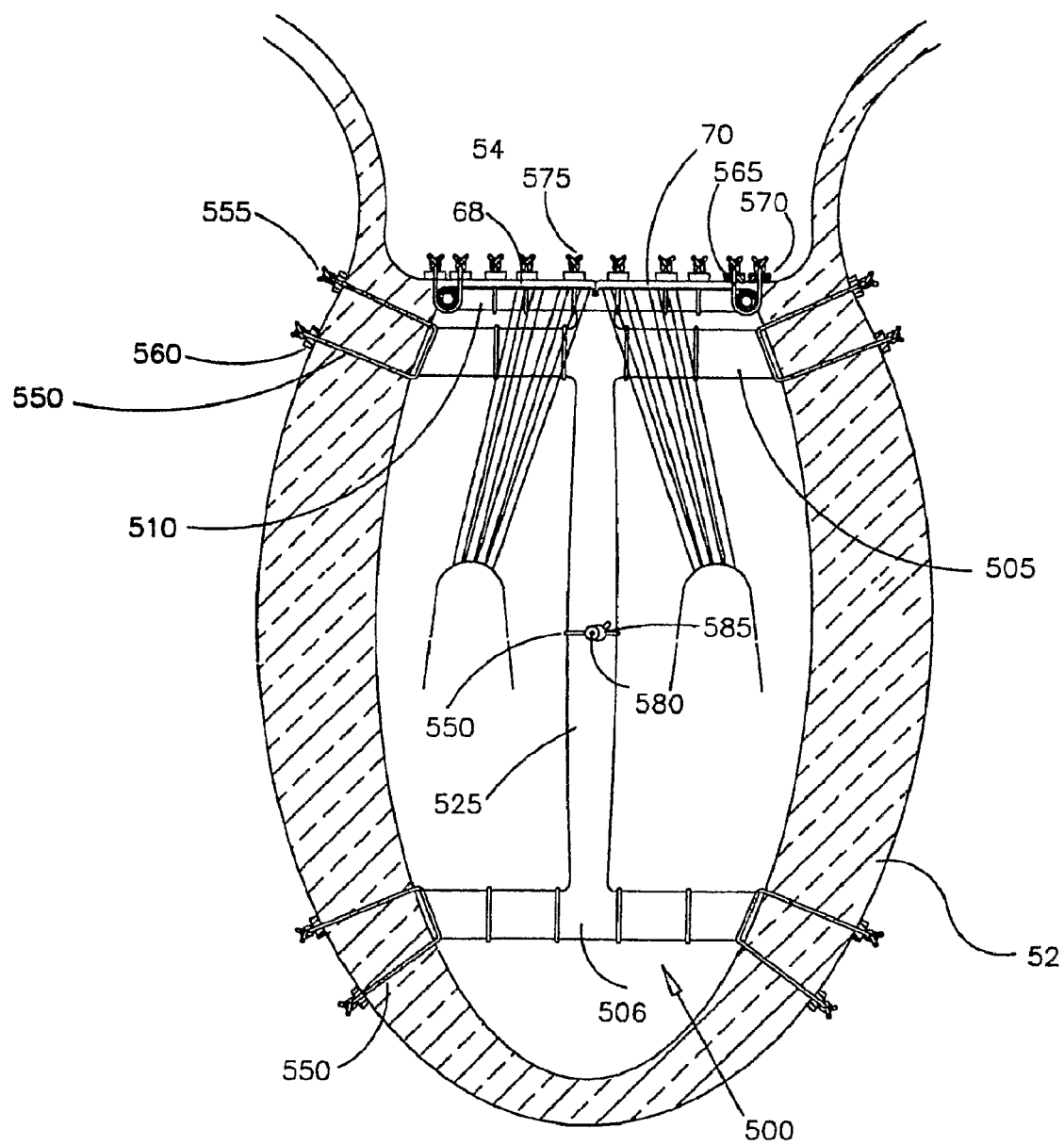
FIG. 40 is a long axis cross-sectional view of the left ventricle and left atrium taken along line RR of FIG. 39.

FIG. 40 shows a long axis cross-sectional view of the left ventricle and left atrium taken along line RR of FIG. 39. Annuloplasty ring 510 is mounted sub-annularly using sutures 565, supported by pledgets 570 and terminated with knots 575. An advantage of this device is that it may be implanted by passage through the mitral valve, obviating the need to open the left ventricle.

The invention claimed is:

1. An apparatus implantable in a heart ventricle comprising:
   a frame configured to engage an inner circumferential periphery of a ventricle and to expand and contract between an expanded state corresponding to a desired end diastolic diameter of a ventricle and a contracted state corresponding to a desired end systolic diameter of the ventricle; and
   assisting means operatively associated with the frame for mechanically assisting movement of the ventricle toward both an end systolic diameter during systole and an end diastolic diameter during diastole.

2. The apparatus of claim 1 further comprising means operatively associated with the frame for limiting the ventricle to a select end diastolic internal diameter.

3. The apparatus of claim 1 wherein the assisting means is integrally formed with the frame.

4. A method of treating cardiac disease comprising:
   surgically accessing a ventricle;
   inserting within the ventricle a resilient band comprising, at least one spring element operatively associated axially with the resilient band to allow axial stretching and compression of the resilient band, the resilient band being configured to limit the ventricle to a select end diastolic internal diameter, the resilient band further comprises a mitral annuloplasty ring extending axially of the resilient band with the resilient band formed into a loop;
   placing the resilient band into contact with the inner circumferential periphery of the ventricle;
   forming the resilient band into a loop of a diameter about equal to an end diastolic diameter of an inner circumferential periphery of the ventricle; and
   attaching the mitral annuloplasty ring to the myocardium below but proximate the mitral annulus.

5. The method of claim 4 wherein the resilient band includes at least one circumferential ligature operatively associated with the resilient band, the circumferential ligature having opposing free ends, the method further comprising:
   forming the resilient band into a loop by tying the opposing free ends of the ligature together.

6. An apparatus implantable in a heart ventricle comprising:
   a bistable element configured to engage an inner circumferential periphery of a ventricle, the bistable element having a contracted stable state and an expanded stable state corresponding to a desired end systolic diameter and an end diastolic diameter, respectively.

7. The apparatus of claim 6 wherein the bistable element comprises a plurality of longitudinal bands each having a top and a bottom end, the top ends of the longitudinal bands being joined by a top circumferential band extending therebetween and the bottom ends of the longitudinal bands being joined by a bottom circumferential band extending therebetween.

8. The apparatus of claim 7 further comprising the bottom circumferential band being configured to perform as a spring.

9. The apparatus of claim 7 further comprising a mitral annuloplasty ring extending axially from a top of the bistable element, the bistable element and the mitral annuloplasty ring being configured so that with the bistable element attached to myocardium defining the inner circumferential periphery of a left ventricle, the mitral annuloplasty ring is below but proximate the mitral annulus.

10. The apparatus of claim 9 wherein at least one of the top and bottom circumferential bands is split across its circumferences to define a C-shaped band.

11. The apparatus of claim 6 further comprising means operatively associated with the bistable element for limiting the expanded stable state of the bistable element to a select diameter.

12. The apparatus of claim 6 wherein the bistable element is configured to self-bias between the expanded and contracted bistable states when circumferentially deflected beyond a select point toward the other of the bistable states.

13. The apparatus of claim 6 having a generally elliptical profile in the expanded state and a generally hour-glass profile in the contracted state generally conforming to an ideal ventricle shape during end diastole and end systole, respectively.

14. A method of augmenting systolic contraction and diastolic relaxation of a heart ventricle comprising:
   providing a bistable element configured to engage an inner circumferential periphery of a ventricle, the bistable element having a contracted stable state and an expanded stable state corresponding to a desired end systolic diameter and end diastolic diameter, respectively;
   surgically accessing the ventricle;
   inserting the bistable element within the ventricle; and
   attaching the bistable element to a portion of myocardium defining the inner circumferential periphery of the ventricle.

15. The method of claim 14 further comprising limiting the expanded stable state of the bistable element to a select diameter.

16. An apparatus implantable in a heart ventricle comprising:
   a resilient band;
   a spring element operatively associated axially with the resilient band;
   means for joining the ends of the resilient band into a circle; the resilient band being configured, with the ends joined, to engage an inner circumferential periphery of a ventricle, with the spring, element in a relaxed state during diastole of the ventricle;
   means operatively associated with the resilient band for limiting the ventricle to a select end diastolic internal diameter; and
   a mitral annuloplasty ring extending axially of the resilient band with the resilient band formed into a circle.

17. The apparatus of claim 16 further comprising a biocompatible sheath around the resilient band and spring element.

18. The apparatus of claim 16 further comprising the spring element being integrally formed of the resilient band.

19. A method of treating cardiac disease comprising:
   a) providing a resilient hand having at least one spring element operatively associated axially with the resilient band to allow axial stretching and compression of the resilient hand and means for limiting axial stretching of the resilient band to a select diameter, comprising a mitral annuloplasty ring extending axially of the resilient band with the resilient band formed into a circle;
   b) surgically accessing a left ventricle of a heart;
   c) placing the resilient band into contact with the inner circumferential periphery of the ventricle;
   d) forming the resilient hand into a loop of a diameter about equal to an end diastolic diameter of an inner circumferential periphery of the ventricle; and
   e) attaching the resilient band loop to the myocardium defining the inner circumferential periphery of the ventricle; and
   f) attaching the mitral annuloplasty ring to the myocardium below but proximate the mitral annulus.

20. The method of claim 19 wherein the resilient band includes at least one circumferential ligature operatively associated with the resilient band, the circumferential ligature having opposing free ends, step d) further comprising:
   forming the resilient band into a loop by tying the opposing free ends of the ligature together.

* * * * *